United States Patent
Eiceman et al.

(10) Patent No.: US 12,159,774 B2
(45) Date of Patent: Dec. 3, 2024

(54) APPARATUS AND METHOD FOR AGRICULTURAL CONTAMINANT DETECTION

(71) Applicant: Arrowhead Center, Inc., Las Cruces, NM (US)

(72) Inventors: Gary A. Eiceman, Las Cruces, NM (US); Jennifer J. Randall, Las Cruces, NM (US); Gyoungil Lee, Las Cruces, NM (US); Alexandre Tarassov, Seven Fields, PA (US)

(73) Assignee: Arrowhead Center, Inc., Las Cruces, NM (US)

( * ) Notice: Subject to any disclaimer, the term of this patent is extended or adjusted under 35 U.S.C. 154(b) by 0 days.

(21) Appl. No.: 18/391,303

(22) Filed: Dec. 20, 2023

(65) Prior Publication Data
US 2024/0128068 A1    Apr. 18, 2024

Related U.S. Application Data

(63) Continuation of application No. 18/116,076, filed on Mar. 1, 2023, now Pat. No. 11,862,447.
(Continued)

(51) Int. Cl.
*H01J 49/10* (2006.01)
*G01N 33/02* (2006.01)
*H01J 49/00* (2006.01)

(52) U.S. Cl.
CPC .......... *H01J 49/0031* (2013.01); *G01N 33/02* (2013.01); *H01J 49/10* (2013.01)

(58) Field of Classification Search
CPC .... H01J 49/0031; H01J 49/10; H01J 49/0404; H01J 49/0422; G01N 33/02
(Continued)

(56) References Cited

U.S. PATENT DOCUMENTS

| 9,899,196 B1 | 2/2018 | Cody |
| 2005/0167583 A1 | 8/2005 | Miller et al. |

(Continued)

FOREIGN PATENT DOCUMENTS

| CN | 109075016 B | 3/2021 |
| WO | 0108197 A1 | 2/2001 |

(Continued)

OTHER PUBLICATIONS

Dart , "VAPUR-Model API-Interfaces", https://www.environmental-expert.com/products/vapur-model-api-interfaces-604018, Downloaded Mar. 2022.

Ewing, Robert G., et al., "Direct Real-Time Detection of Vapors from Explosive Compounds", Anal. Chem., vol. 85, No. 22, 2013, 10977-10983.

(Continued)

*Primary Examiner* — Kiet T Nguyen
(74) *Attorney, Agent, or Firm* — Peacock Law P.C.; Deborah A. Peacock; Marco H. Santamaria

(57) ABSTRACT

An apparatus for detecting a substance comprising a direct analysis in real time apparatus; a neutral excluder; a mass spectrometer; and a vessel in. The apparatus may also comprise a separator, a gas, an alcohol, a filter, and a pump. The apparatus may also comprise electrodes in communication with the direct analysis in real time apparatus and the neutral excluder. A method for detecting a substance comprising contacting the substance with a direct analysis in real time apparatus ion stream; forming an ion and a neutral particle; flowing the ion and the neutral particle into a neutral excluder; contacting the ion and the neutral particle with a gas; and flowing the ion into a mass spectrometer.

19 Claims, 42 Drawing Sheets

Related U.S. Application Data

(60) Provisional application No. 63/315,384, filed on Mar. 1, 2022.

(58) Field of Classification Search
USPC .................................. 250/288, 281, 282
See application file for complete search history.

(56) References Cited

U.S. PATENT DOCUMENTS

| | | |
|---|---|---|
| 2010/0078553 A1 | 4/2010 | Corso et al. |
| 2010/0132561 A1 | 6/2010 | Bromberg et al. |
| 2012/0080593 A1 | 4/2012 | Miki |
| 2013/0001413 A1 | 1/2013 | Witham |
| 2014/0302616 A1 | 10/2014 | Sipila et al. |
| 2015/0235830 A1 | 8/2015 | Murase |
| 2017/0200596 A1 | 7/2017 | Makarov et al. |
| 2018/0238776 A1* | 8/2018 | Karancsi ............. H01J 49/0027 |
| 2020/0355646 A1 | 11/2020 | Swager et al. |
| 2021/0215638 A1 | 7/2021 | Jones et al. |

FOREIGN PATENT DOCUMENTS

| | | |
|---|---|---|
| WO | 2007056488 A1 | 5/2007 |
| WO | 2015189552 A2 | 12/2015 |
| WO | 2018150193 A1 | 8/2018 |

OTHER PUBLICATIONS

Fenn, John B., "Ion Formation from Charged Droplets: Roles of Geometry, Energy, and Time", J Am Soc Spectrom, vol. 4, 1993, 524-535.

Lee, G., et al., "Ion Mobility Spectrometry toward Real-time Detection of Aflatoxin", Poster presentation at 27th ISIMS Conference, Calgary, Alberta, Canada Jul. 2018, Jul. 2018.

Saucedo, Griselda A., et al., "Evaluation of GC/DMS for Detection of Aflatoxin", Poster presentation at Society of Invitro Biology, Tucson, Arizona Jun. 2015, Jun. 2015.

Sheibani, Ali, et al., "Determination of aflatoxins B1 and B2 using ion mobility spectrometry", Talanta, vol. 75, No. 1, 2008, 233-238.

Shephard, Gordon S., "Aflatoxin analysis at the beginning of the twenty-first century", Analytical and Bioanalytical Chemistry, vol. 395, No. 5, 2009, 1215-1224.

Sukumar, H., et al., "Paper spray ionization with ion mobility spectrometry at ambient pressure", Int. J. Ion Mobil. Spec., vol. 14, 2011, 51-59.

Wang, Xinxin, et al., "Rapid determination of chemical composition in the particulate matter of cigarette mainstream smoke", Talanta, vol. 217, 121060, Apr. 23, 2020.

Wollnick, H., et al., "A Curtain-Gas Filter that Widely Protects Mass Spectrometers from Neutral Molecule Contaminations", Poster presentation, 9th Workshop on Harsh-Environment Mass Spectrometry, St. Pete Beach, Florida, USA, Sep. 15-18, 2013, 2013.

* cited by examiner

| Total Aflatoxin by ELISA (ppb) | | | |
|---|---|---|---|
|  | Bag A | Bag B | Bag C |
| Sample 1 | 21.60 | 21.30 | 21.67 |
| Sample 2 | 22.63 | 24.37 | 41.50 |
| Average | 22.12 | 24.84 | 31.58 |

FIG. 4

| Compound | Formula | Moral Mass | Vapor Pressure mm Hg at 25°C | Solubility mg/L at 25°C |
|---|---|---|---|---|
| B1 | $C_{17}H_{12}O_6$ | 312.277 | $2.65 \times 10^{-10}$ | 16.14 |
| B2 | $C_{17}H_{14}O_6$ | 314.293 | $1.65 \times 10^{-10}$ | 24.9 |
| G1 | $C_{17}H_{12}O_7$ | 328.276 | $5.86 \times 10^{-11}$ | 477 |
| G2 | $C_{17}H_{14}O_7$ | 330.292 | $7.68 \times 10^{-11}$ | $3.73 \times 10^{+3}$ |
| Low Vapor Pressure Compounds as Reference | | | | |
| RDX | $C_3H_6N_6O_6$ | 222.117 | $4.10 \times 10^{-9}$ at 20°C | - |
| PETN | $C_5H_8N_4O_{12}$ | 316.135 | $1.36 \times 10^{-7}$ | - |
| Tetryl | $C_7H_5N_5O_8$ | 287.144 | $1.2 \times 10^{-7}$ | - |

FIG. 8

| Particle size [μm] | Aflatoxin B1 [ppb] |
|---|---|
| > 250 | 108 |
| 125 < sample < 250 | 243 |
| < 125 | 800 |

FIG. 32

APPARATUS AND METHOD FOR AGRICULTURAL CONTAMINANT DETECTION

CROSS-REFERENCE TO RELATED APPLICATIONS

This application is a continuation of U.S. application Ser. No. 18/116,076 filed on Mar. 1, 2023, entitled "APPARATUS AND METHOD FOR AGRICULTURAL CONTAMINANT DETECTION", which application claims priority to and the benefit of the filing of U.S. Provisional Patent Application No. 63/315,384, entitled "APPARATUS AND METHOD FOR AGRICULTURAL CONTAMINANT DETECTION", filed on Mar. 1, 2022, and the specifications and drawings thereof are incorporated herein by reference.

BACKGROUND OF THE INVENTION

Field of the Invention (Technical Field)

Embodiments, of the present invention relate to detection of contaminants in agricultural products.

BACKGROUND ART

Contaminants may be present in any number of agricultural setting, processes, and/or products. For example, aflatoxins are produced from fungi (*Aspergillus flavus* and *Aspergillus parasiticus*) that can enter food supplies through ordinary practices of production. Owing to known or anticipated health effects from aflatoxin consumption, levels of contaminants in processed foods are strongly regulated by government oversight. Some compelling physical properties of contaminant compounds include vapor pressures and solubility. For example, for some nuts, including pistachio nuts that contain high amounts of oils and lipids, traditional measurement methods such electrospray ionization are not effective.

Mass spectrometers with atmospheric pressure ionization ("API") sources can detect levels of some explosives with extraordinarily low vapor pressures. Contaminant vapor pressures are 10 times to 10,000 times lower than those for explosives (e.g., pentaerythritol tetranitrate ("PETN"), 2,4,6-trinitrophenylmethylnitramine ("Tetryl"), and 1,3,5-trinitro-1,3,5-triazinane ("RDX")). This expectation is consistent with experience that temperatures of 250° C. or higher are needed for gas chromatographic analyses of contaminants. High temperatures can result in thermal decomposition of contaminant and consequently analysis methods have migrated to solution-based methods such as liquid extraction with liquid chromatography. These are unsuitable for agricultural product monitoring.

BRIEF SUMMARY OF THE INVENTION

Embodiments of the present invention relate to an apparatus for detecting a substance, the apparatus comprising: a direct analysis in real time apparatus; and a neutral excluder in communication with the direct analysis in real time apparatus. In another embodiment, the apparatus further comprises a separator in communication with the neutral excluder. In another embodiment, the apparatus further comprises a mass spectrometer in communication with the neutral excluder. In another embodiment, the apparatus further comprises a vessel in communication with the neutral excluder. In another embodiment, the apparatus further comprises a gas. In another embodiment, the gas comprises air.

In another embodiment, the apparatus further comprises an alcohol. In another embodiment, the apparatus further comprises a filter in communication with the neutral excluder. In another embodiment, the apparatus further comprises a pump in communication with the neutral excluder. In another embodiment, the apparatus further comprises an electrode in communication with the direct analysis in real time apparatus. In another embodiment, the apparatus further comprises an electrode in communication with the neutral excluder. In another embodiment, the neutral excluder further comprises an insulator. In another embodiment, the substance comprises a dust.

Embodiments of the present invention relate to a method for detecting a substance, the method comprising: contacting the substance with a direct analysis in real time apparatus ion stream; ionizing the substance to form an ion and a neutral particle; and flowing the ion and the neutral particle into a neutral excluder. In another embodiment, the method further comprises contacting the ion and the neutral particle with a gas. In another embodiment, the gas comprises air.

In another embodiment, the method further comprises separating the ion from the neutral particle. In another embodiment, the method further comprises flowing the ion into a mass spectrometer. In another embodiment, the method further comprises flowing the substance into a separator. In another embodiment, the method further comprises applying a current to the neutral excluder.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 4 is a table of the total aflatoxin in pistachio-associated dust according to an embodiment of the present invention;

FIG. 8 is a table showing selected chemical and physical properties of aflatoxins according to an embodiment of the present invention;

FIG. 32 is a table showing example results from studies on dust size according to an embodiment of the present invention;

DETAILED DESCRIPTION OF THE INVENTION

Figure 1:
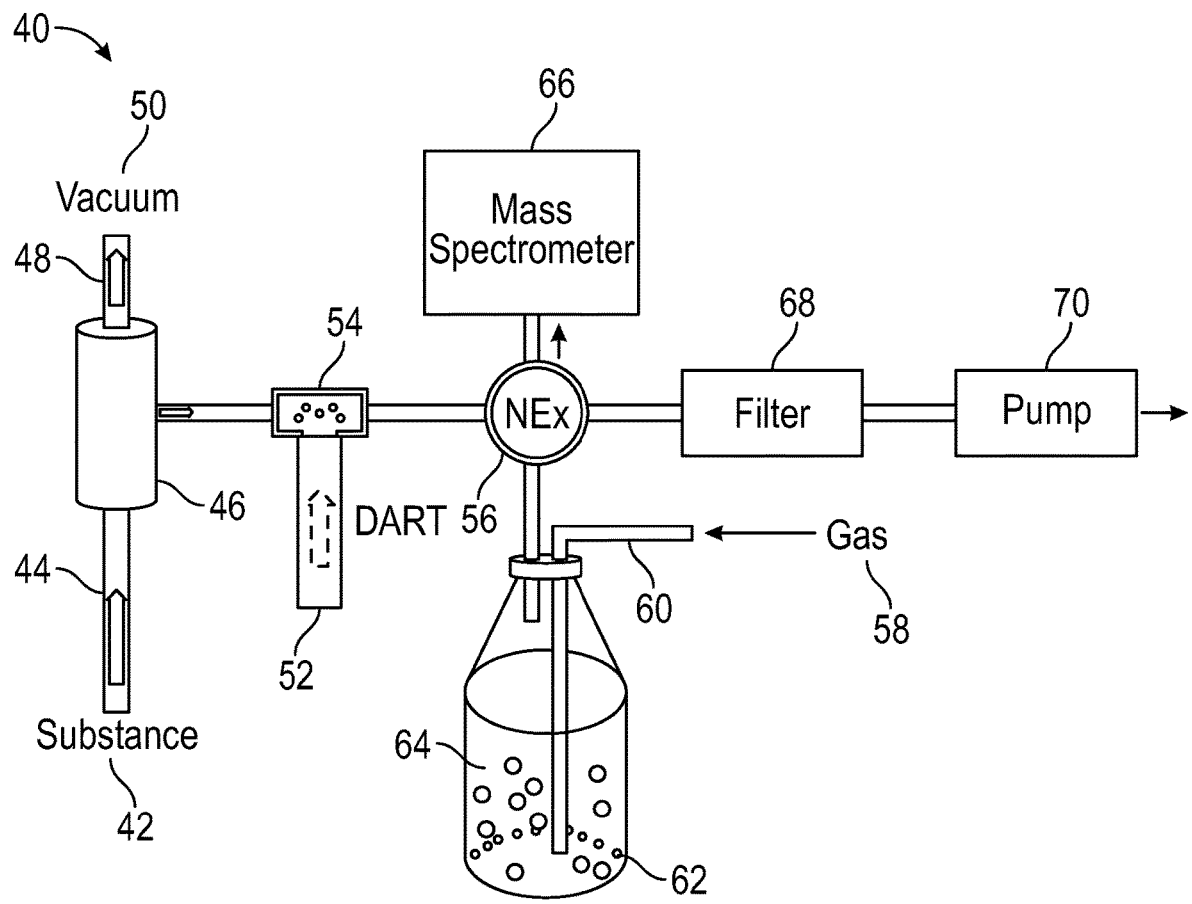
FIG. 1 is a diagram of direct analysis in real time neutral excluder with mass spectrometry ("DART-neutral excluder-MS") apparatus with a modifier after DART, a neutral excluder interface, and an attached separator according to an embodiment of the present invention.

An embodiment of the present invention is directed to an apparatus (also referred to herein as a DART-neutral excluder-MS) for detecting a substance, the apparatus comprising: a direct analysis in real time (DART) apparatus; a mass spectrometer (MS) apparatus; and a neutral excluder. The neutral excluder may be in communication with the DART and MS to form a direct analysis in real time-neutral excluder-mass spectrometer (DART-neutral excluder-MS).

An embodiment of the present invention is also directed to an apparatus for detecting a substance, the apparatus comprising: a mesh; direct analysis in real time with mass spectrometry ("DART-MS") apparatus; a DART-MS substance chamber; and a DART-MS interface comprising a purified gas flow. The mesh may comprise a metal or other suitable material. In another embodiment, the DART-MS substance chamber may comprise: a housing; a cavity in communication with a mass spectrometry ("MS") inlet; an orifice directing a direct analysis in real time ("DART") ion stream; an orifice for receiving a substance; and a cavity for receiving a substance and DART ion stream wherein the DART ion stream contacts the substance.

In one embodiment, the apparatus for detecting a substance comprises: a direct analysis in real time with mass spectrometry ("DART-MS") apparatus; a neutral excluder; a particulate filter; an after-DART modifier; and a vessel. The neutral excluder may comprise: a first housing having a first end and second end and forming an outer cavity space; a second housing with a first end and second end, disposed within the outer cavity space, and forming a middle cavity space; a third housing with a first end and second end, disposed within the middle cavity, and forming an inner cavity; a first inlet for receiving ionized matter; and a second inlet for receiving gas. The apparatus may further comprise an organic solvent. The apparatus may further comprise a suction pump.

An embodiment of the present invention is directed to an apparatus for detecting a substance, the apparatus comprising: a direct analysis in real time (DART) apparatus; a mass spectrometer (MS) apparatus; and a neutral excluder. The DART may be a pulsed DART or a continuous flow DART. The neutral excluder may be in communication with the DART and MS to form a direct analysis in real time-neutral excluder-mass spectrometer (DART-neutral excluder-MS). The neutral excluder may comprise: a housing; a first inlet for receiving purified air and/or alcohol vapors; a second inlet for receiving a substance; a first outlet in communication with a pump; and a second outlet in communication with a mass spectrometer. The housing may comprise a first half comprising the first inlet and second outlet. The housing may also comprise a second half comprising the second inlet and first outlet. The DART-neutral excluder-MS may further comprise a conduit in communication with the first outlet and a suction pump. The DART-neutral excluder-MS may also comprise a vessel containing a vaporous alcohol in communication with the first inlet.

The apparatus may comprise: a mesh; direct analysis in real time with mass spectrometry ("DART-MS") apparatus; a DART-MS substance chamber; and a DART-MS interface comprising a purified gas flow. The DART-MS substance chamber may comprise: a housing; a cavity in communication with an MS inlet; an orifice directing a DART ion stream; an orifice for receiving a substance; and a cavity for receiving a substance and DART ion stream wherein the DART ion stream contacts the substance. The purified gas may comprise, but not be limited to, air, nitrogen, helium, or a combination thereof. The DART-MS substance chamber may be in communication with the DART-MS interface. The DART-MS substance chamber and DART-MS interface may be at least partially disposed between the DART and MS. Gas may be flowed through the apparatus to purify the substance.

An embodiment of the present invention is also directed to a method for detecting a substance, the method comprising: flowing a substance into a DART ion stream; generating a mixture comprising ionic and non-ionic particulate matter in a gas phase; flowing the mixture into a neutral excluder; contacting the mixture with an alcohol; separating the ionic particulate matter from the non-ionic particular matter in the mixture; and flowing the ionic particulate matter into a mass spectrometer.

In one embodiment, the method comprises: flowing a substance in an after-DART modifier; contacting the substance with a DART ion stream to form a gaseous ionized substance; flowing the gaseous ionized substance into a neutral excluder to form a purified gaseous ionized substance and neutral matter; and flowing neutral matter into a particulate filter. The method may further comprise flowing the purified gaseous ionized substance into a mass spectrometer. The method may further comprise flowing a gas through the neutral excluder.

An embodiment of the present invention is also directed to a method for detecting a substance, the method comprising: flowing a dust into a DART ion stream to form a mixture of ionic and non-ionic matter in a gas phase; flowing the mixture into a neutral excluder; contacting the mixture with purified air; separating the ionic matter from the non-ionic matter in the mixture; and flowing the ionic matter into a mass spectrometer. The purified air may comprise alcohol vapors and the alcohol may comprise methanol, ethanol, 2-propanol, butanol, or a combination thereof. The method may further comprise applying a negative pressure and/or suction to flow the mixture into and/or through the neutral excluder. The method may further comprise: flowing the mixture into a first channel; flowing ions and/or ionic matter into a second channel; flowing purified air into a third channel; contacting the ions and/or ionic matter with the purified air an intersection of the second and third channel to form a flow of ions and/or ionic matter in purified air, and flowing the ionic matter in purified air out of the neutral excluder.

In one embodiment, the method may comprise: contacting a substance with a mesh; at least partially disposing the mesh and substance within a DART-MS substance chamber; contacting the substance with a DART-MS ion stream to produce gaseous ion of the substance; flowing the gaseous ions of the substance into a DART-MS interface; and isolating the gaseous ions of the substance from other matter. The gaseous ions of the substance may be isolated by a flow of gas, e.g., purified gas. In another embodiment, the method further comprises flowing the isolated gaseous ions of the substance into a mass spectrometer. Gas may be flowed through the apparatus and may purify the substance. The substance may be organic or not organic. The substance may comprise agricultural products including nuts and/or other agricultural products as described herein. The nuts may comprise, but not be limited to, pistachios. The substance may comprise agricultural dust including, but not limited to, pistachio dust.

The mass spectrometer may be any mass spectrometer including, but not limited to, an ion mobilization mass spectrometer, a tandem mass spectrometer, a Fourier-transform mass spectrometer, an ion cyclotron resonance mass spectrometer, a matrix-assisted laser desorption and/or ionization time-of-flight mass spectrometer, an inductively coupled plasma mass spectrometer, or a combination thereof. The mass spectrometer may be used in combination with a gas chromatograph, a liquid chromatograph, or a combination thereof. The apparatus may also further comprise a liquid and/or gas chromatograph.

The apparatus may prevent fouling of the mass spectrometer. Fouling may be prevented by separating ions from neutral particles in the neutral excluder to reduce the amount of substance and/or increase the purity and/or proportion of ions entering the mass spectrometer.

The apparatus may be capable of continuous monitoring. Continuous monitoring may be performed by disposing a substance into the apparatus at a constant rate. The apparatus may also be a capable of interval monitoring, batch monitoring, pulse monitoring, or a combination thereof. Interval monitoring, batch monitoring, pulse monitoring may be performed by disposing a substance into the apparatus at intervals, as a batch of substance, or as a pulse of substance, respectively.

The term "substance" is defined as a chemical compound. The chemical compound may be in an ionized state and may be a solid, liquid, and/or gas. The substance may be particulate matter, a dust, a fine, an extract, or a combination thereof.

The term "dust" is defined as the particles generated by agricultural processing. "Dust" may include, but is not limited to, nut dust, nut particles, nut particulate matter, particulate nut waste; and dust, particles, particulate matter, and particulate waste from any of the following: agricultural products, nuts, including but not limited to, pistachios, almonds, pecans, walnuts, cashews, peanuts, other nut products; corn, soybean, wheat, grains, sorghum, rice, chili, coffee, grapes, cocoa, cacao, legumes, chocolate, potatoes, tuberous vegetables, cereal, figs, animal feed other agricultural products; carrots, radishes, cassava, artichoke, jicama, sweet potato, yam, taro, water chestnut, turmeric, *ginseng*, lotus root, ginger, groundnut, turnips, parsley root, alfalfa, barley, oats, cereals, rye, canola, cottonseed, beets, sugarcane, roughages, pasture grass, hay, silage, straw, cornstalk; or a combination thereof. "Dust" may further include, but is not limited to, shells, shavings, or chaff derived from the substances listed herein. The terms "ion" or "ionic matter" are defined as matter that has a non-neutral charge.

Turning now to the figures, FIG. 1 shows DART-neutral excluder-MS 40 with a modifier after DART and in a curtain gas of neutral excluder. Substance 42 is flowed into separator 46 via conduit 44. Waste is removed from separator 46 via conduit 48 by vacuum 50. Substance 42 then flows into modifier after DART 54. Substance is ionized with DART 52 and flowed to neutral excluder 56. Purified air 58 is flowed through conduit 60 and into vessel 64 where gas 58 contacts alcohol 62 before flowing into neutral excluder 56 to contact and purify substance 42. Waste matter is captured by particulate filter 68. Flow throughout the system is maintained, at least in part, by suction pump 70. Purified ionized substance is flowed into mass spectrometer 66 from neutral excluder 56.

Figure 2:
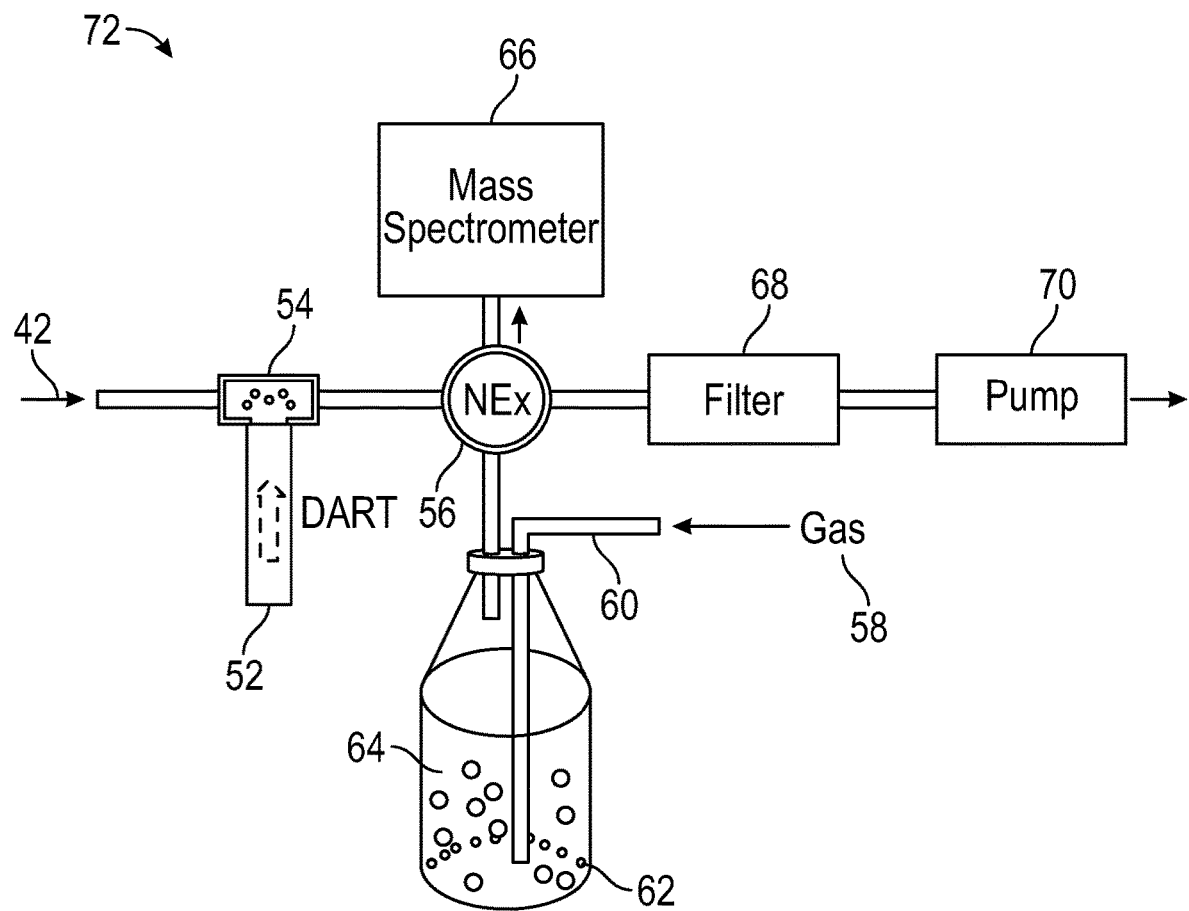
FIG. 2 is a diagram of direct analysis in real time neutral excluder with mass spectrometry ("DART-neutral excluder-MS") apparatus with a modifier after DART and a neutral excluder interface according to an embodiment of the present invention.

FIG. 2 shows DART-neutral excluder-MS 72 with a modifier after DART and in a curtain gas of neutral excluder. Substance 42 is flowed into modifier after DART 54. Substance is ionized with DART 52 and flowed to neutral excluder 56. Purified air 58 is flowed through conduit 60 and into vessel 64 where gas 58 contacts alcohol 62 before flowing into neutral excluder 56 to contact and purify substance 42. Waste matter is captured by filter 68. Flow throughout the system is maintained, at least in part, by suction pump 70. Purified ionized substance is flowed into mass spectrometer 66 from neutral excluder 56.

Figure 3:
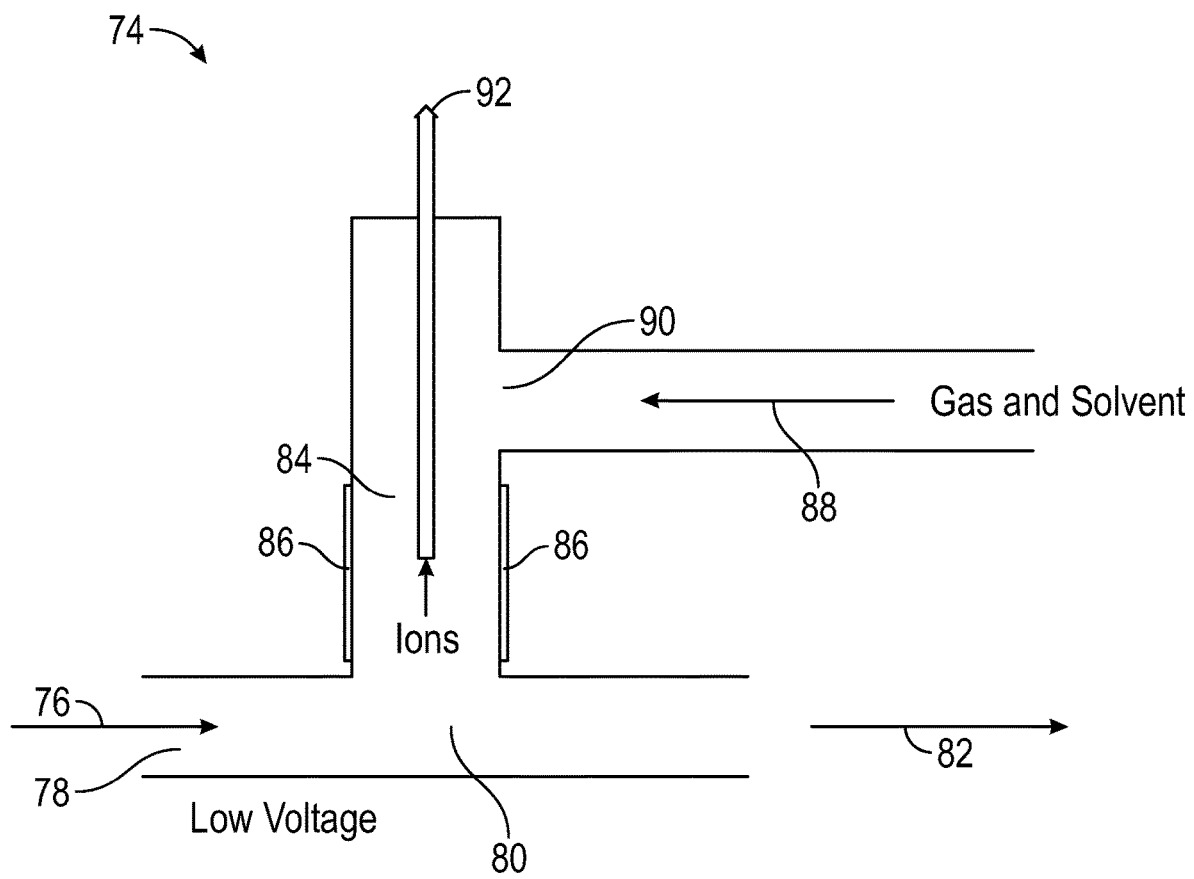
FIG. 3 is a cutaway diagram of a neutral excluder showing channels within the neutral excluder according to an embodiment of the present invention.

FIG. 3 shows neutral excluder channel system 74 shown with the interior channel regions of a neutral excluder. Gas flow 76 that includes, but is not limited to, dust, aerosols, vapors, and ions enters channel 78. The gas flow bifurcates at channel intersection 80. At least part of gas flow 76 enters channel 84, with remaining gas flow 82 exiting channel 80. Purified air enters through channel 88 and meets with the gas flow at channel intersection 90 to form gas ions in purified air. The gas ions in purified air may then enter a capillary tube channel 92 to be directed to a mass spectrometer for analysis. Neutral excluder channel system 74 is charged to allow the separation of ions from neutral particles and direct ions to capillary tube channel 92. Insulators 86 are disposed along channel 84. Optionally, insulators 86 are ceramic insulator layers.

FIG. 4 shows the total aflatoxin in pistachio-associated dust. Aflatoxin is detected in samples of pistachio-associated dust.

Figure 5:
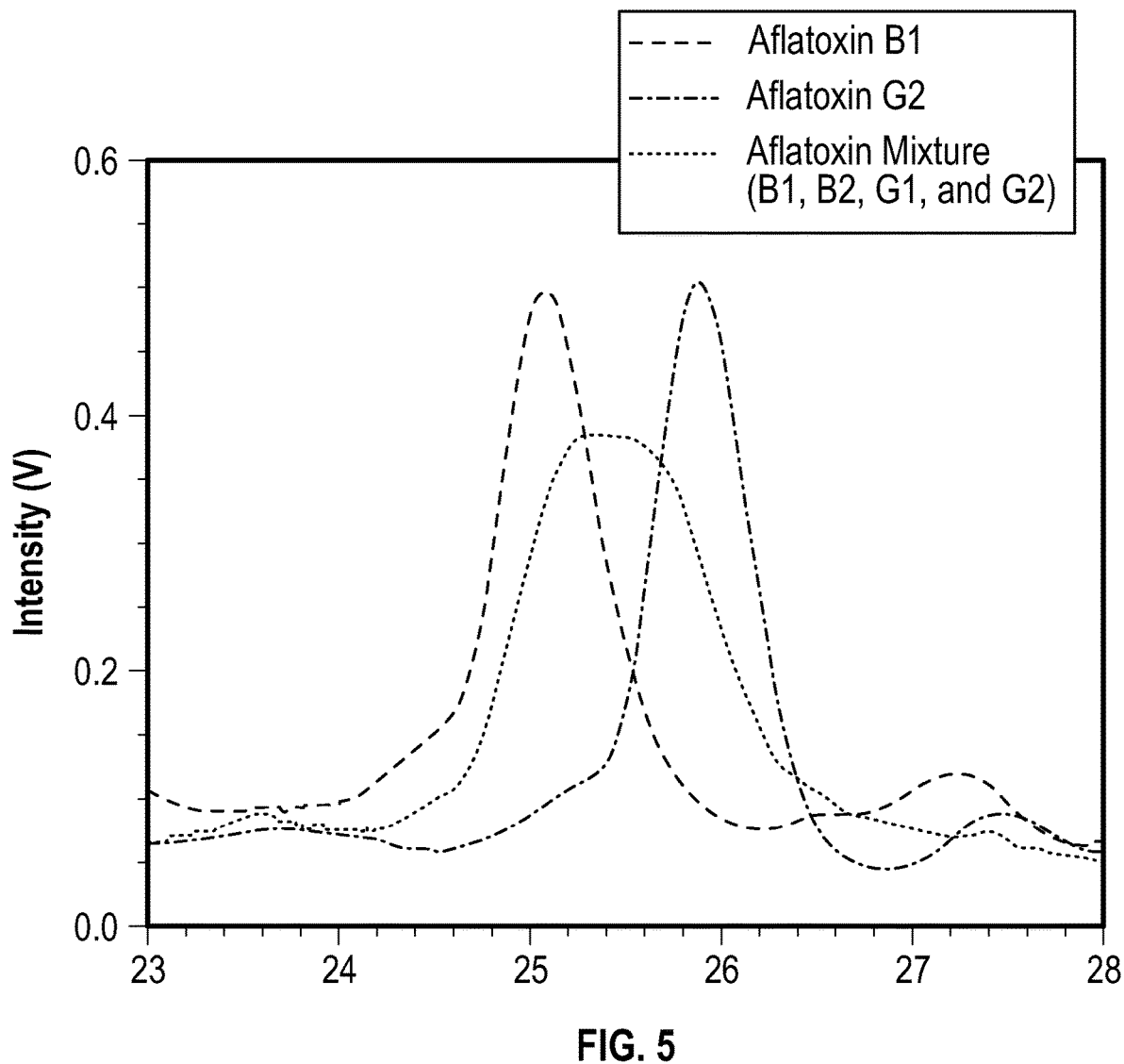
FIG. 5 is a graph of aflatoxin standards for ion mass spectrometry ("IMS") according to an embodiment of the present invention.

FIG. 5 shows aflatoxin standards IMS. Aflatoxins B1 and G2 and an aflatoxin mixture show distinct peaks.

Figure 6:
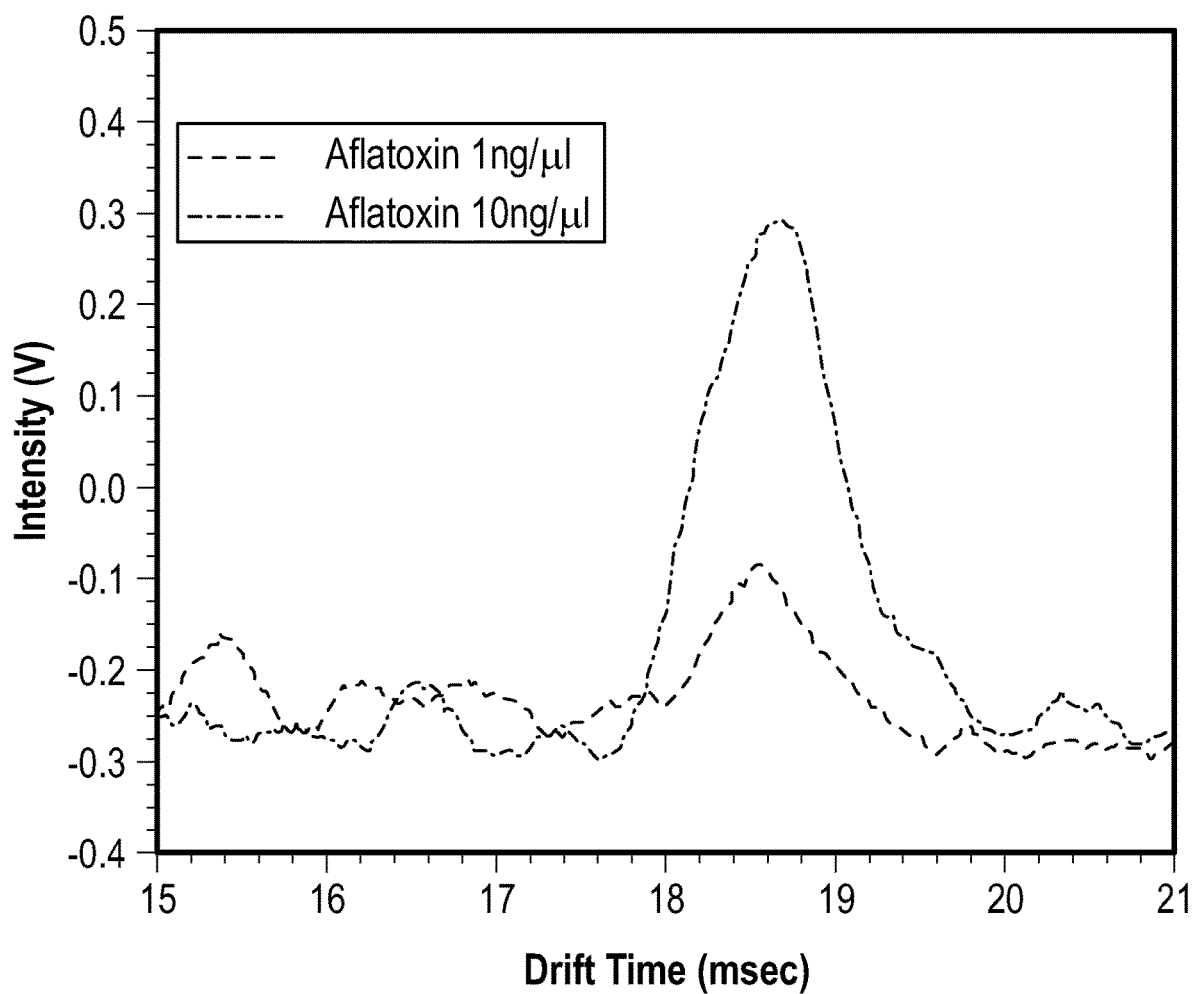
FIG. 6 is a graph showing the detection limit of aflatoxin using mass spectrometry where aflatoxin at 1 ng/μL is equivalent to 1 ppb and aflatoxin at 10 ng/μL is equivalent to 10 ppb according to an embodiment of the present invention.

FIG. 6 shows the detection limit of aflatoxin using mass spectrometry where aflatoxin at 1 ng/μL is equivalent to 1 ppb and aflatoxin at 10 ng/μL is equivalent to 10 ppb. Aflatoxin at 10 ng/μL shows a larger peak than 1 ng/μL.

Figure 7:
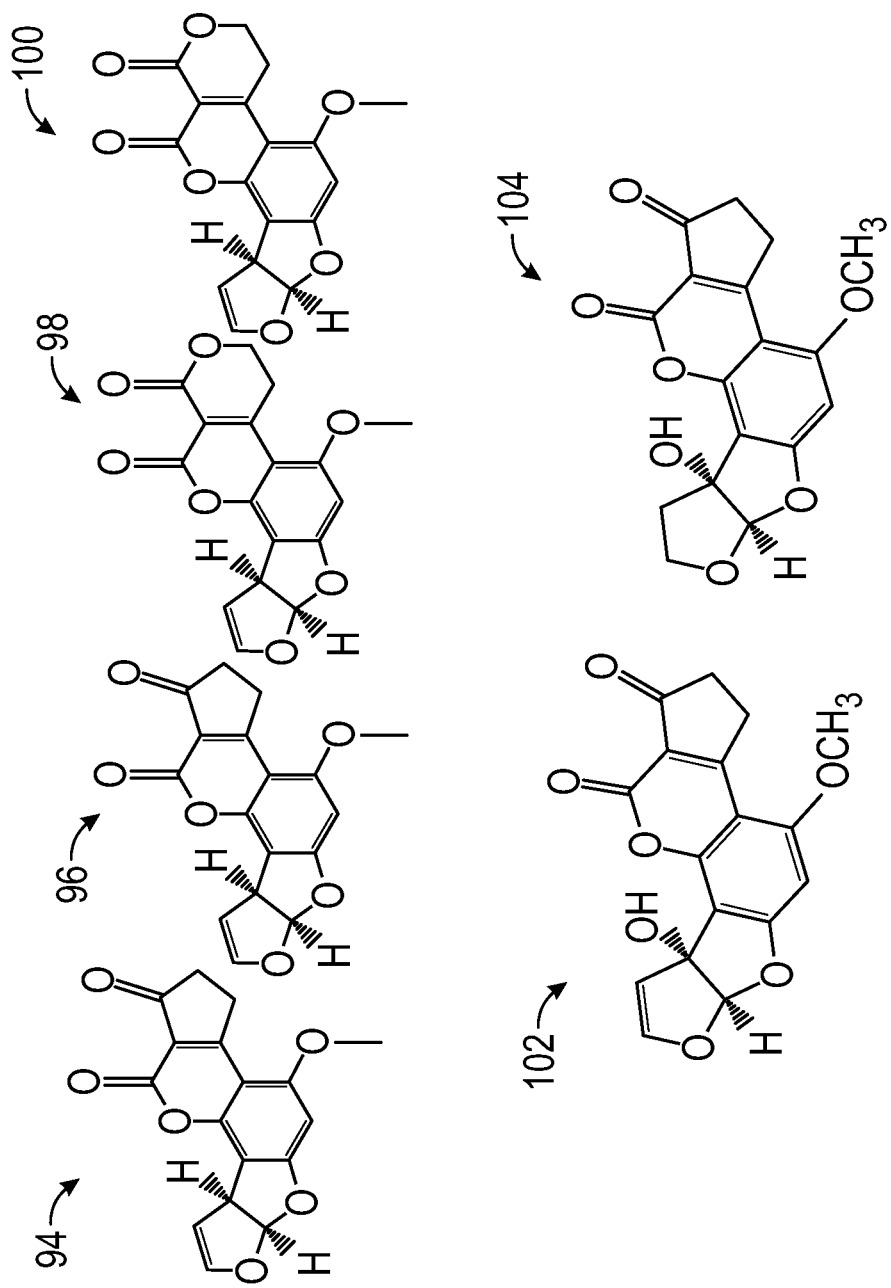
FIG. 7 is a series of illustrations for the chemical structures of key aflatoxins according to an embodiment of the present invention.

FIG. 7 shows the chemical structures of key aflatoxins. Aflatoxins B1 94, B2 96, G1 98, G2 100, M1 102, and M2 104.

FIG. 8 shows the chemical and physical properties of aflatoxins and explosive substances RDX, PETN, and Tetryl. The molar masses and vapor pressures for aflatoxins are similar to the explosive substances.

Figure 9:
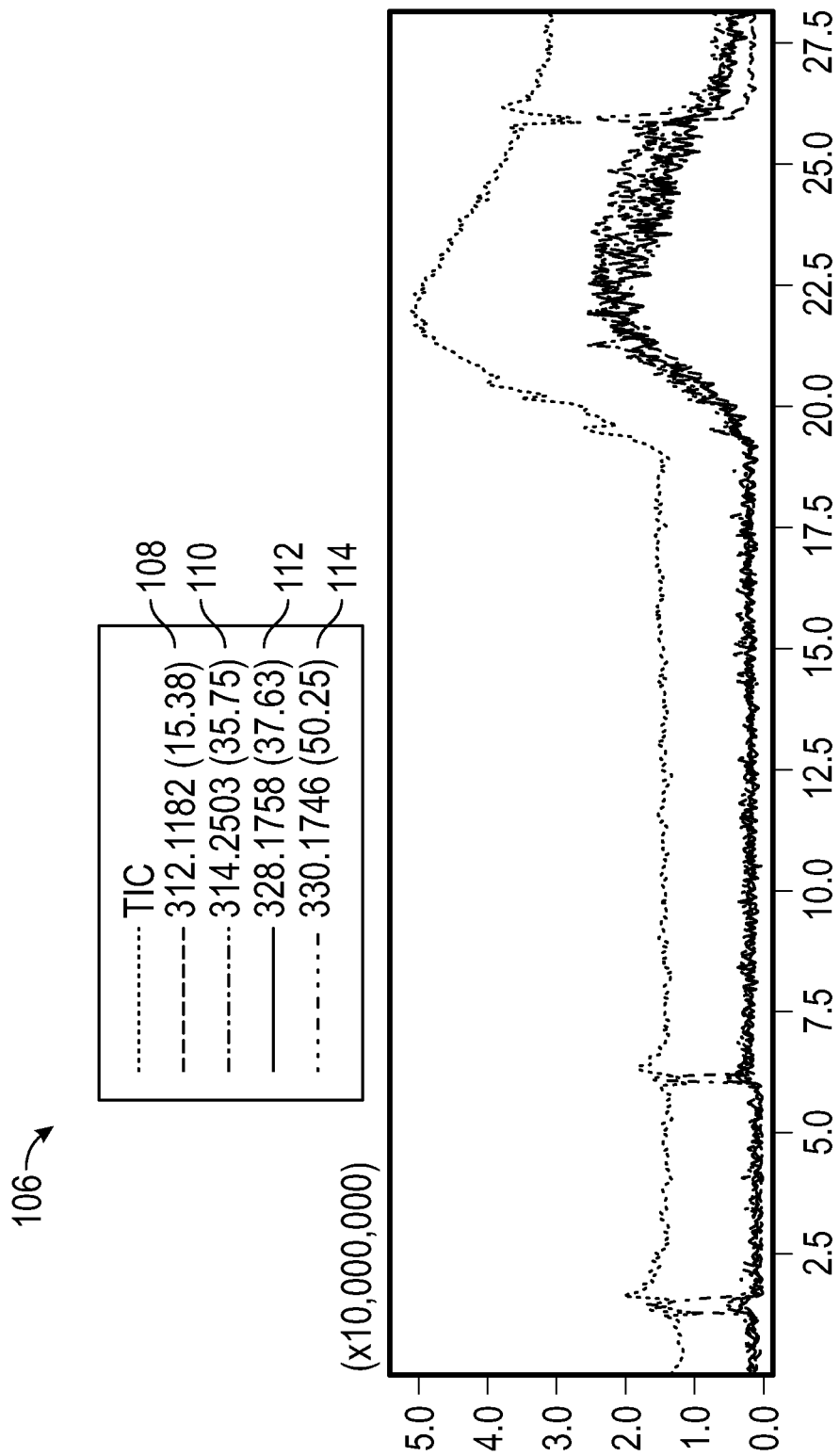
FIG. 9 is a graph showing results from heating a substance spiked with four aflatoxins where there was an increased mass ion intensity for aflatoxins according to an embodiment of the present invention.

FIG. 9 shows results from heating a substance spiked with four aflatoxins where there was an increased mass ion intensity for aflatoxins. Spectra 106 shows peaks for B1 108, B2 110, G1 112, and G2 114.

Figure 10:
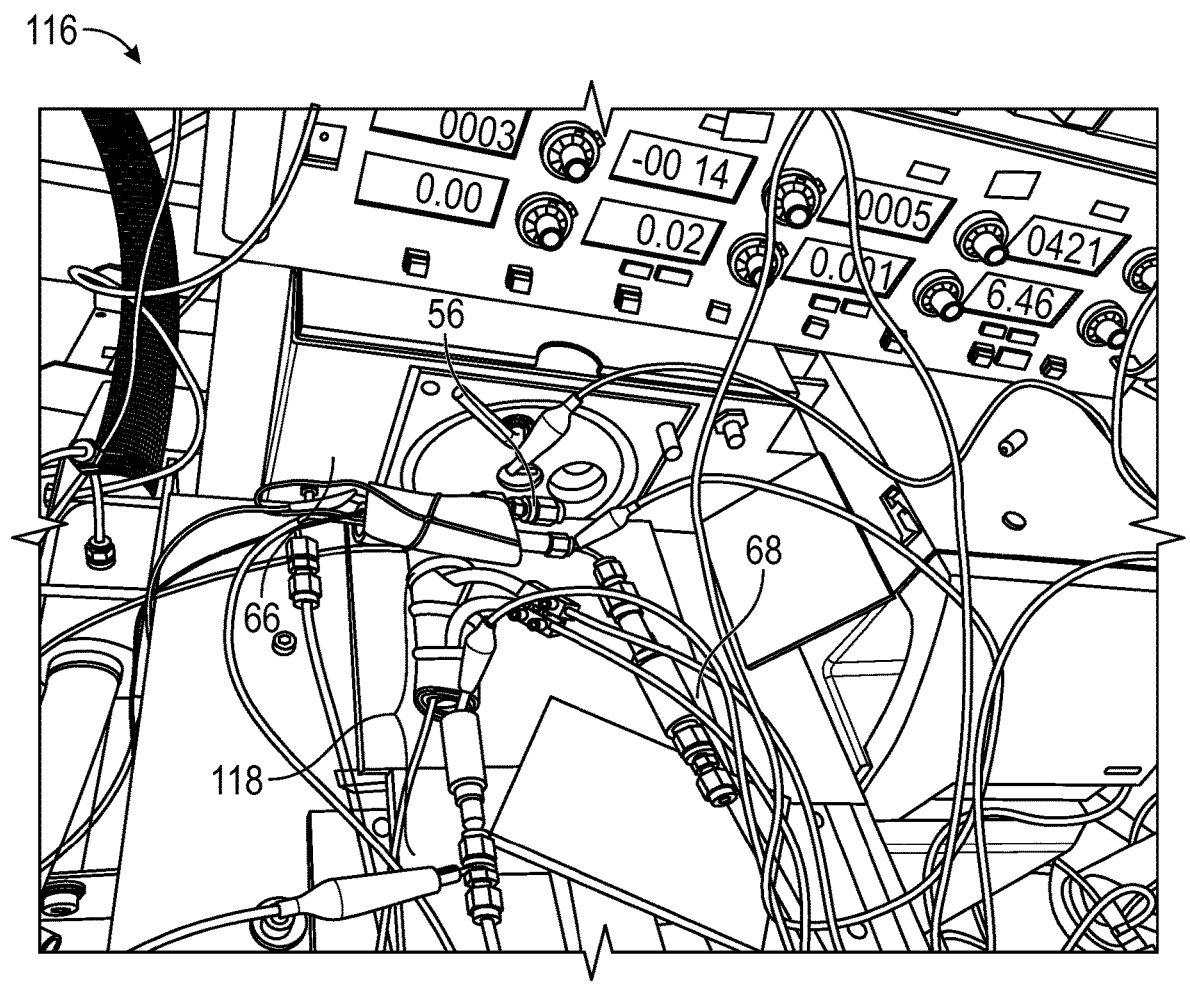
FIG. 10 is a diagram showing a DART-neutral excluder-MS with an attached particle filter according to an embodiment of the present invention.

FIG. 10 shows a DART-neutral excluder-MS 116 with an attached filter. DART 118 is in communication with neutral excluder 56. Neutral excluder 56 is in communication with mass spectrometer 66 and particle 68.

Figure 11A:
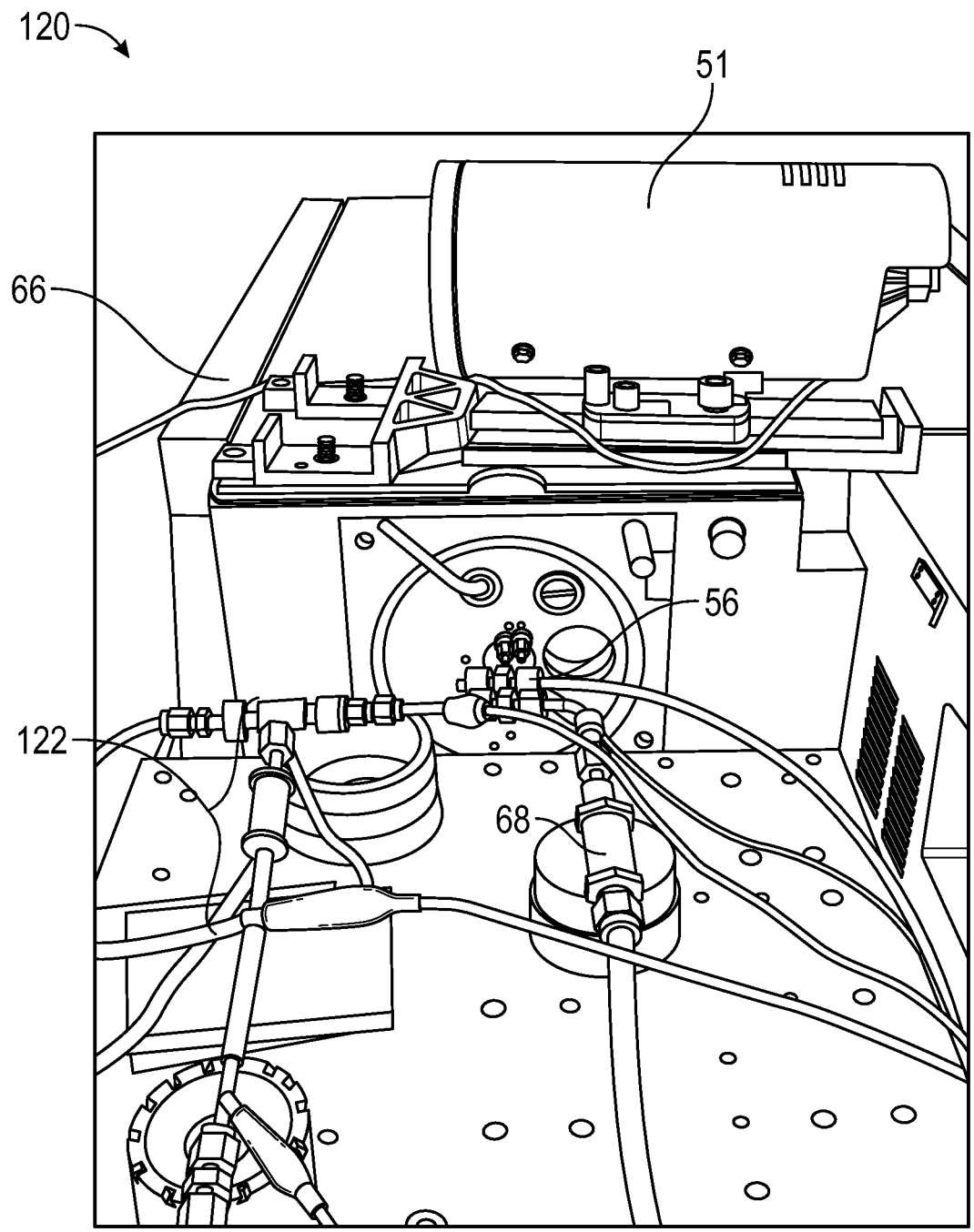
FIG. 11A and FIG. 11B are diagrams showing a DART-neutral excluder-MS with an improved DART and a first-generation DART for reference, and a DART-neutral excluder-MS with a tubular DART, respectively, according to embodiments of the present invention.
Figure 11B:
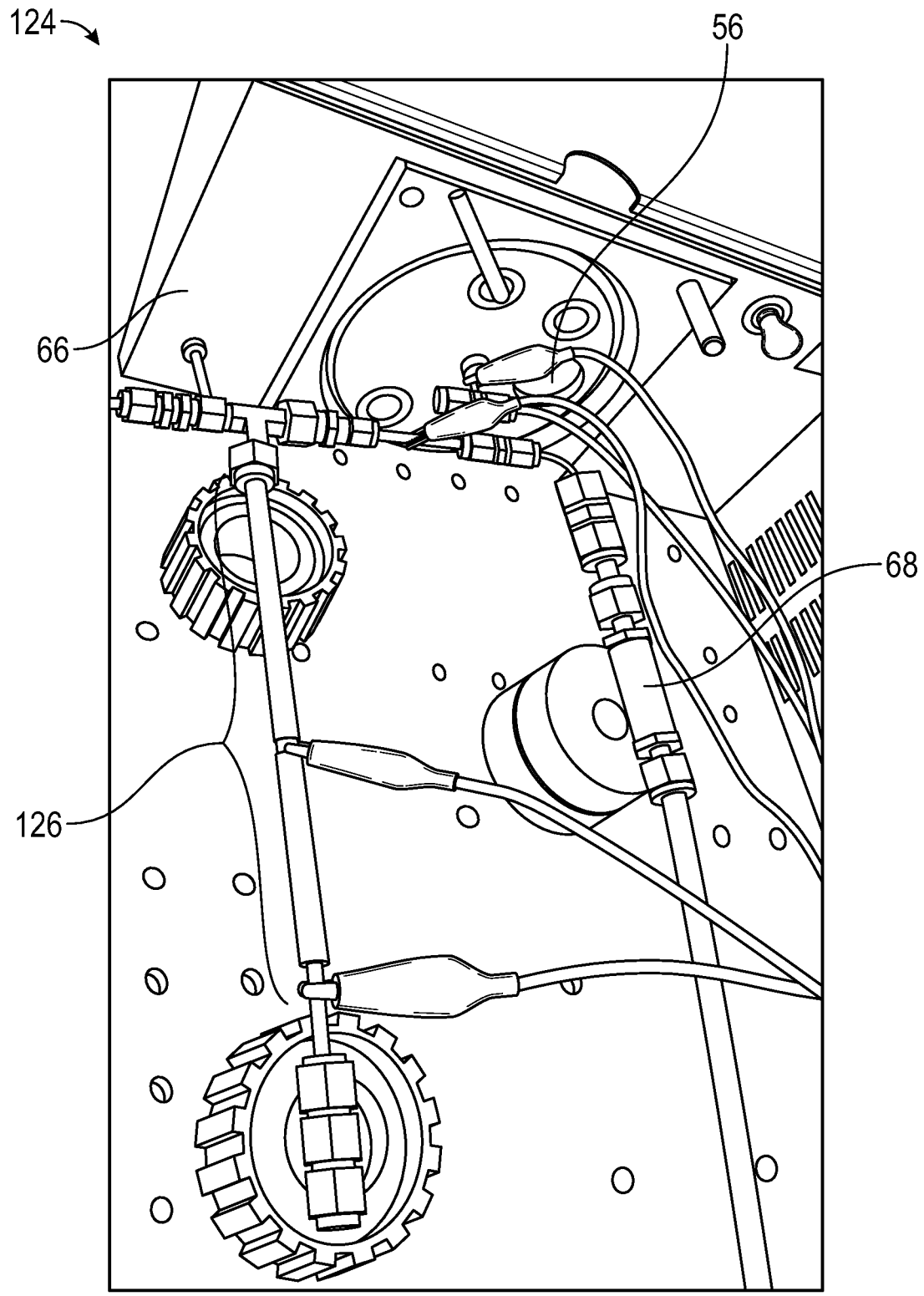

FIG. 11A shows a DART-neutral excluder-MS 120 with an improved DART and a first-generation DART for reference. DART-neutral excluder-MS 120 comprises improved DART 122, mass spectrometer 66, neutral excluder 56, and filter 68. Improved DART 122 is in communication with neutral excluder 56. Neutral excluder 56 is in communication with filter 68 and mass spectrometer 66. First-generation DART 51 is shown for reference and may be used in place of improved DART 122. FIG. 11B shows a DART-neutral excluder-MS 124 with tubular DART 126. DART-neutral excluder-MS 124 comprises tubular DART 126, neutral excluder 56, mass spectrometer 66, and filter 68. Tubular DART 126 is in communication with neutral excluder 56. Neutral excluder 56 is in communication with neutral excluder 66 and filter 68.

Figure 12A:
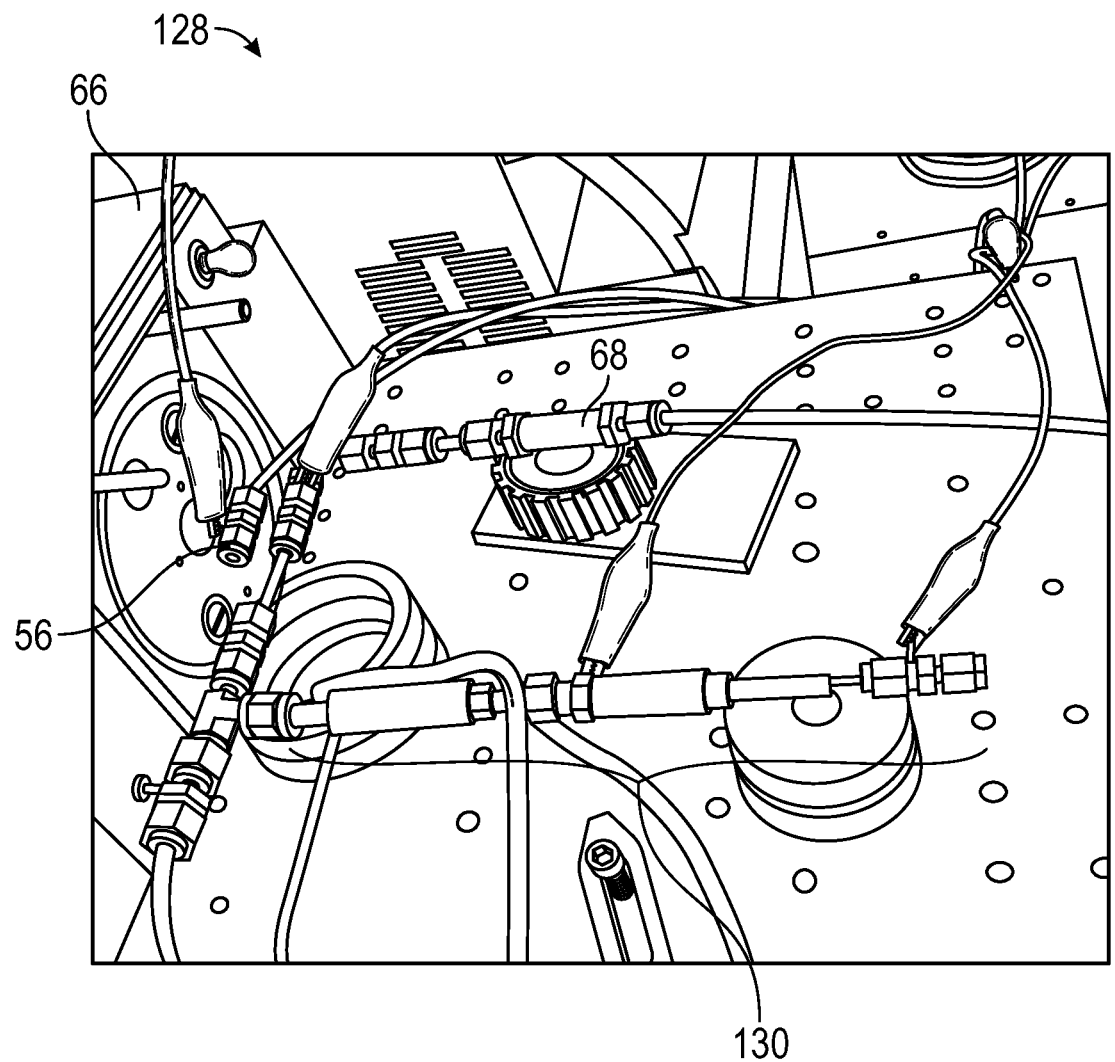
FIG. 12A and FIG. 12B are diagrams showing a DART-neutral excluder-MS with an improved DART embodiments according to embodiments of the present invention.
Figure 12B:
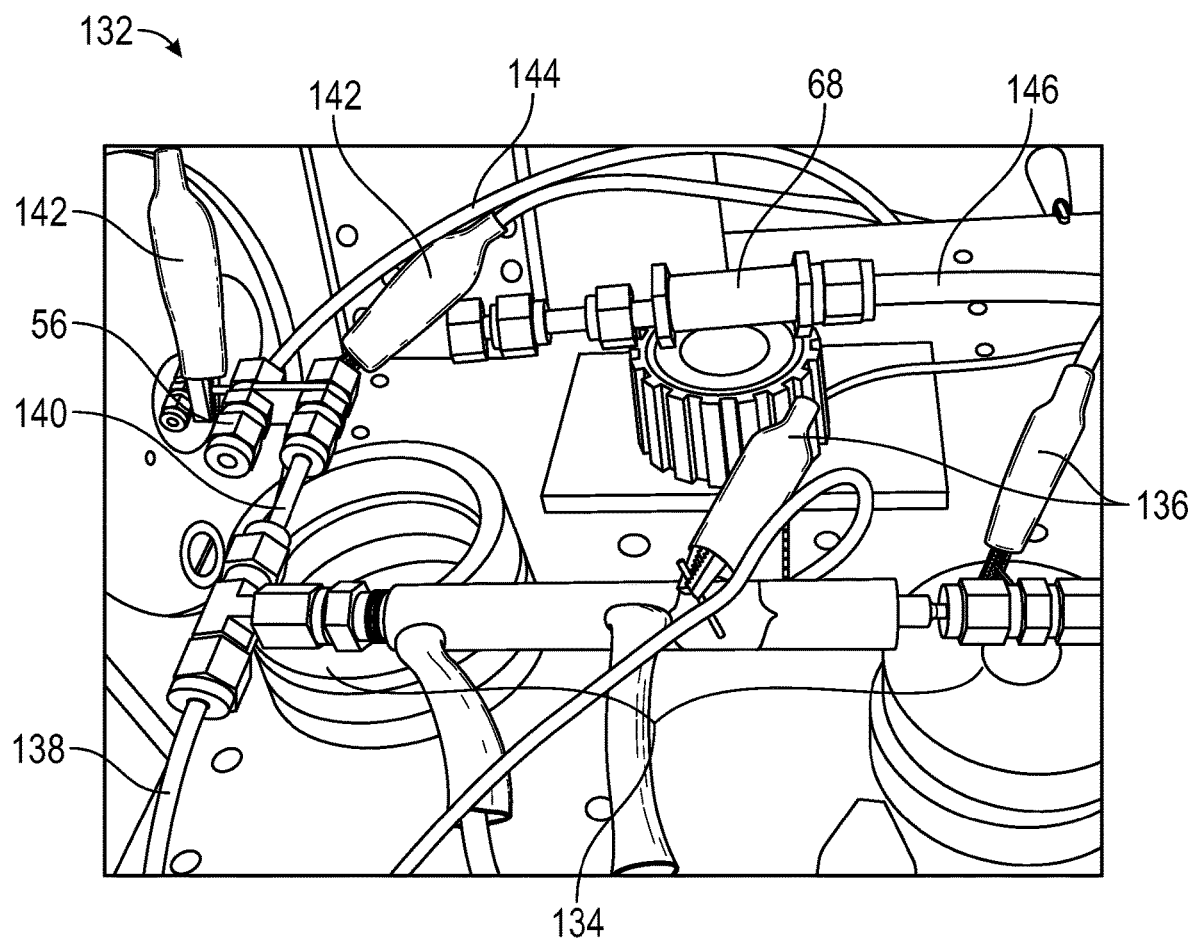

FIG. 12A and FIG. 12B show a DART-neutral excluder-MS with improved DART embodiments. FIG. 12A shows DART-neutral excluder-MS 128 comprising improved DART 130, neutral excluder 56, mass spectrometer 66 and filter 68. Improved DART 130 is in communication with neutral excluder 56. Neutral excluder 56 is in communication with mass spectrometer 66 and filter 68. FIG. 12B shows DART-neutral excluder-MS 132 comprising DART 134, neutral excluder 56, filter 68, conduit 138, conduit 140, conduit 144, conduit 146, electrodes 136, and electrodes 142. Electrodes 136 are attached to DART 134. DART 134 is in communication with conduit 138 and conduit 140. Conduit 140 is in communication with neutral excluder 56. Electrodes 142 are attached to neutral excluder 56. Neutral excluder 56 is in communication with conduit 144, filter 68, and conduit 146. A substance to be analyzed flows into conduit 138 and contacts DART ion stream from DART 134 to form ionized particles. The substance passes through conduit 140 and flows into neutral excluder 56. Air flows into neutral excluder 56 via conduit 144 and neutral excluder 56 separates ions from neutral particles. Ions enter a mass spectrometer and neutral particles enter filter 68 and filtered air passes into conduit 146.

Figure 13:
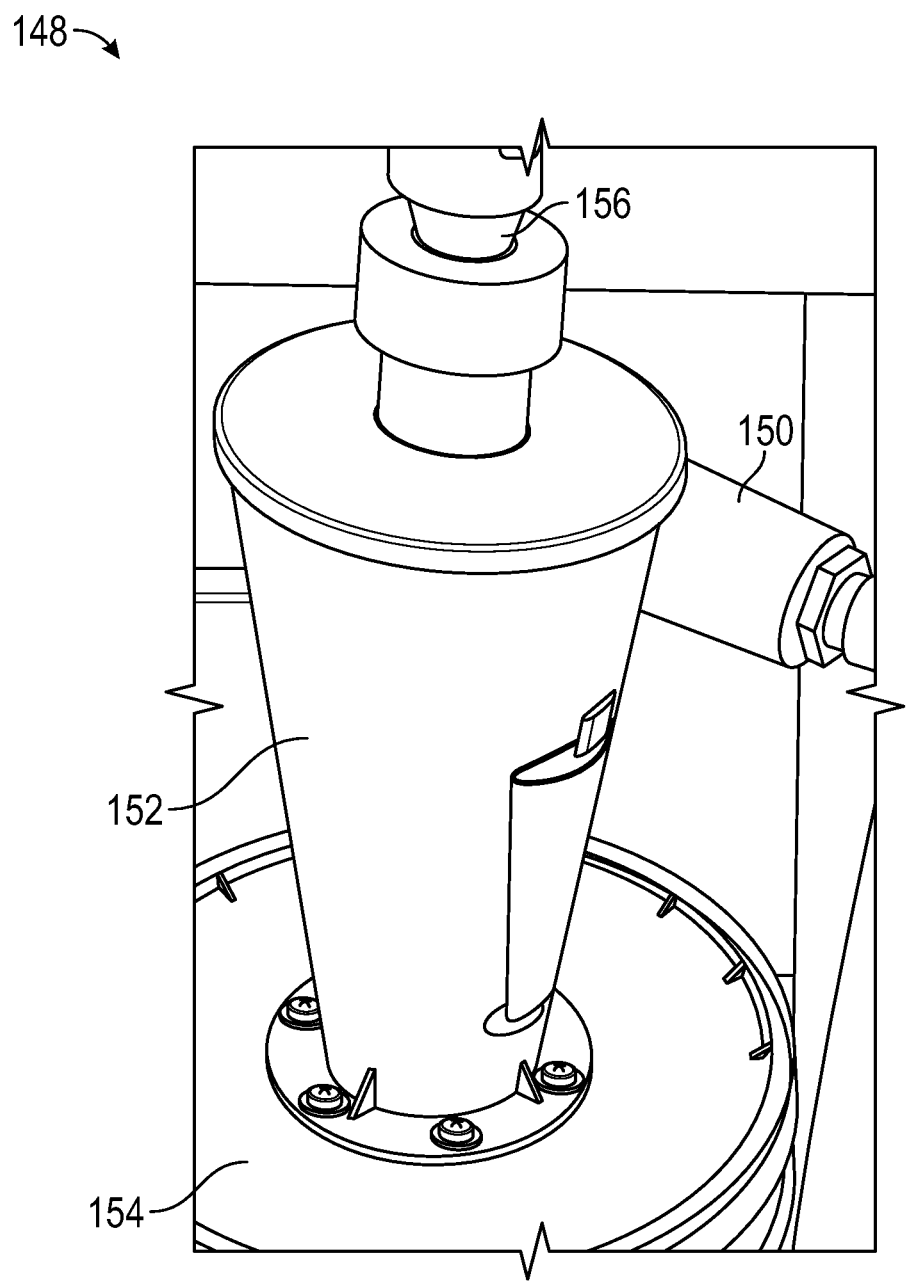
FIG. 13 is a diagram showing a cyclone separator according to an embodiment of the present invention.

FIG. 13 shows a cyclone separator. Cyclone separator 148 comprises input 150, vessel 152, collection bin 154, and outlet 156. Outlet 156 is attached to vessel 152. Vessel 152 is attached to collection bin 154 and outlet 156.

Figure 14A:
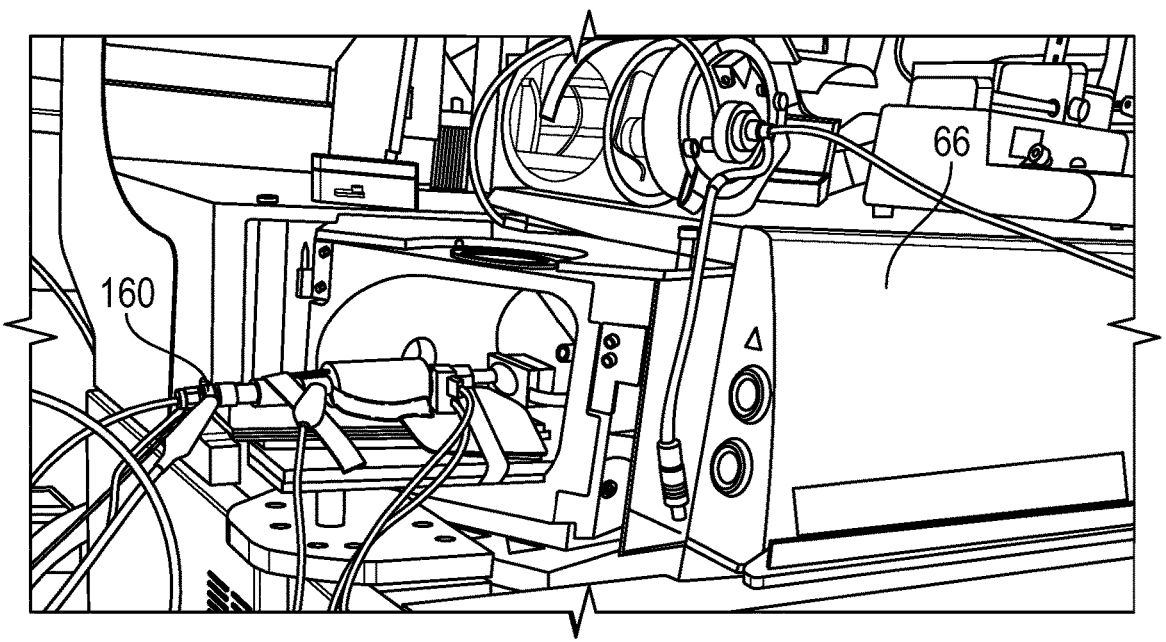
FIG. 14A and FIG. 14B are diagrams showing a DART-neutral excluder-MS and a sample mesh according to embodiments of the present invention.
Figure 14B:
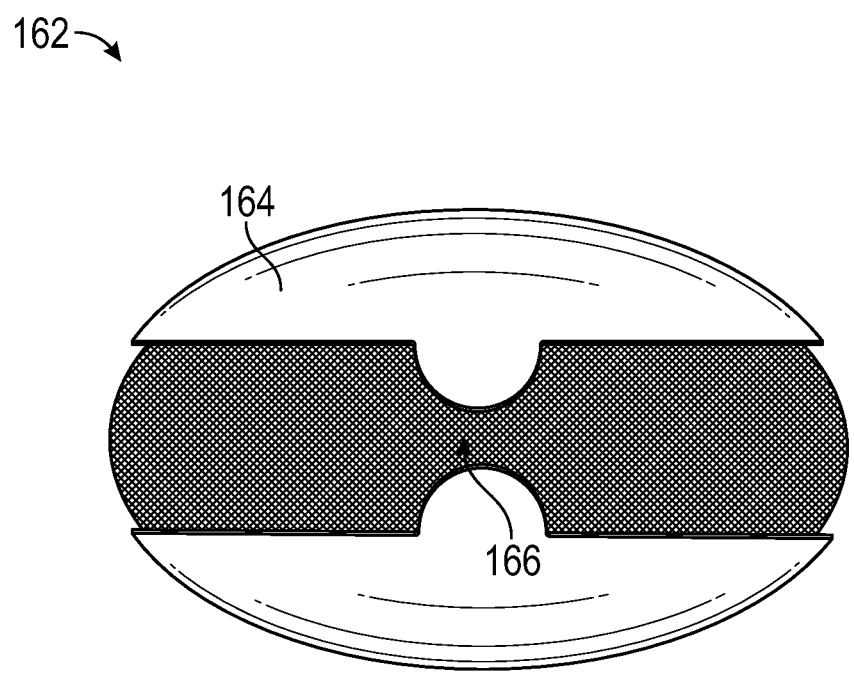

FIG. 14A and FIG. 14B show a DART-neutral excluder-MS and a sample mesh. Setup 158 comprises DART mount 160 and mass spectrometer 66. Sample mount 162 comprises outer plate 164 and mesh 166.

Figure 15:
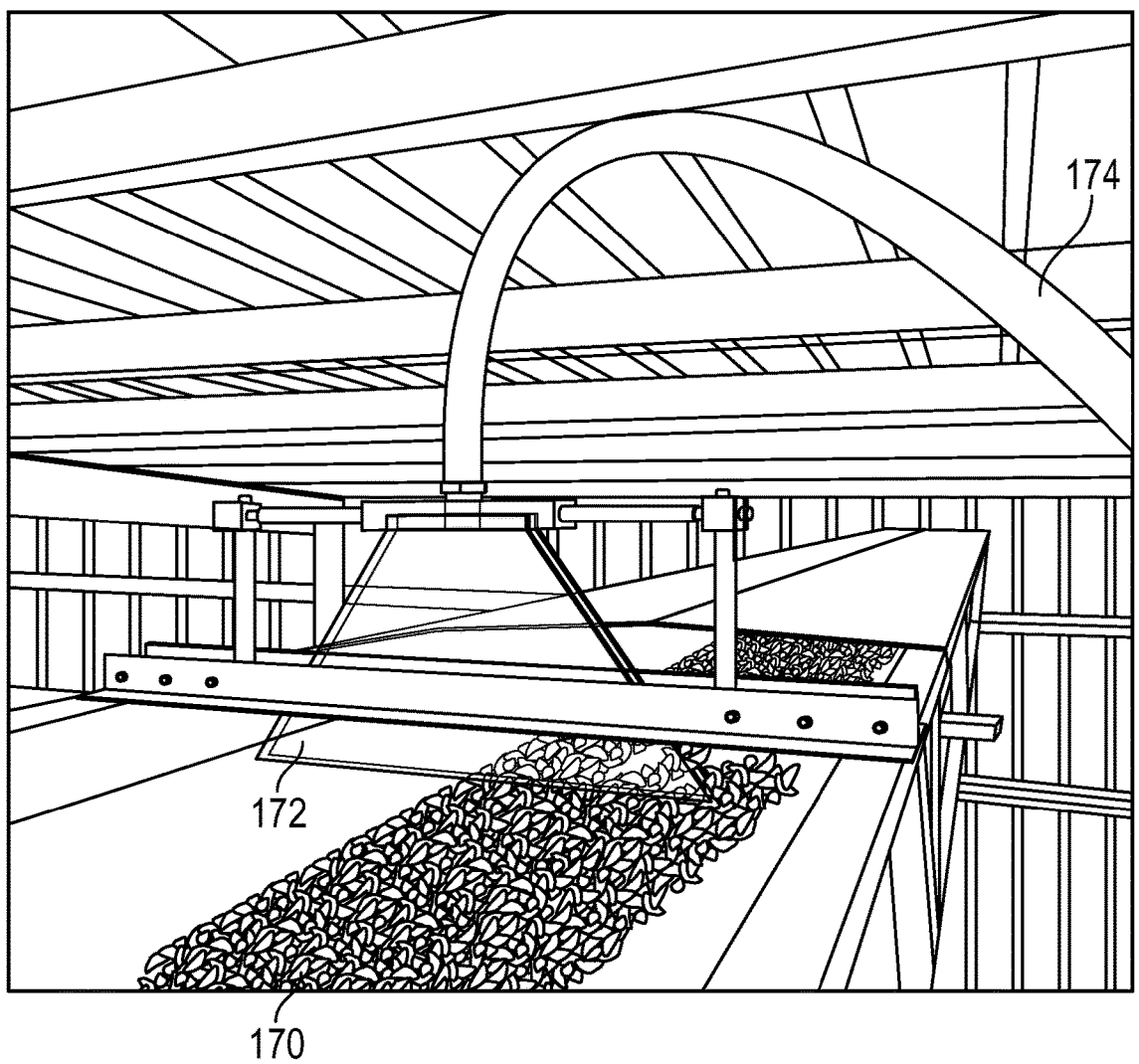
FIG. 15 is a diagram showing dust collection from a pistachio nut production belt according to an embodiment of the present invention.

FIG. 15 shows dust collection from a pistachio nut production belt. Dust collection system 168 comprises inlet cone 172 and conduit 174. Dust is collected from moving pistachio belt 170.

Figure 16:
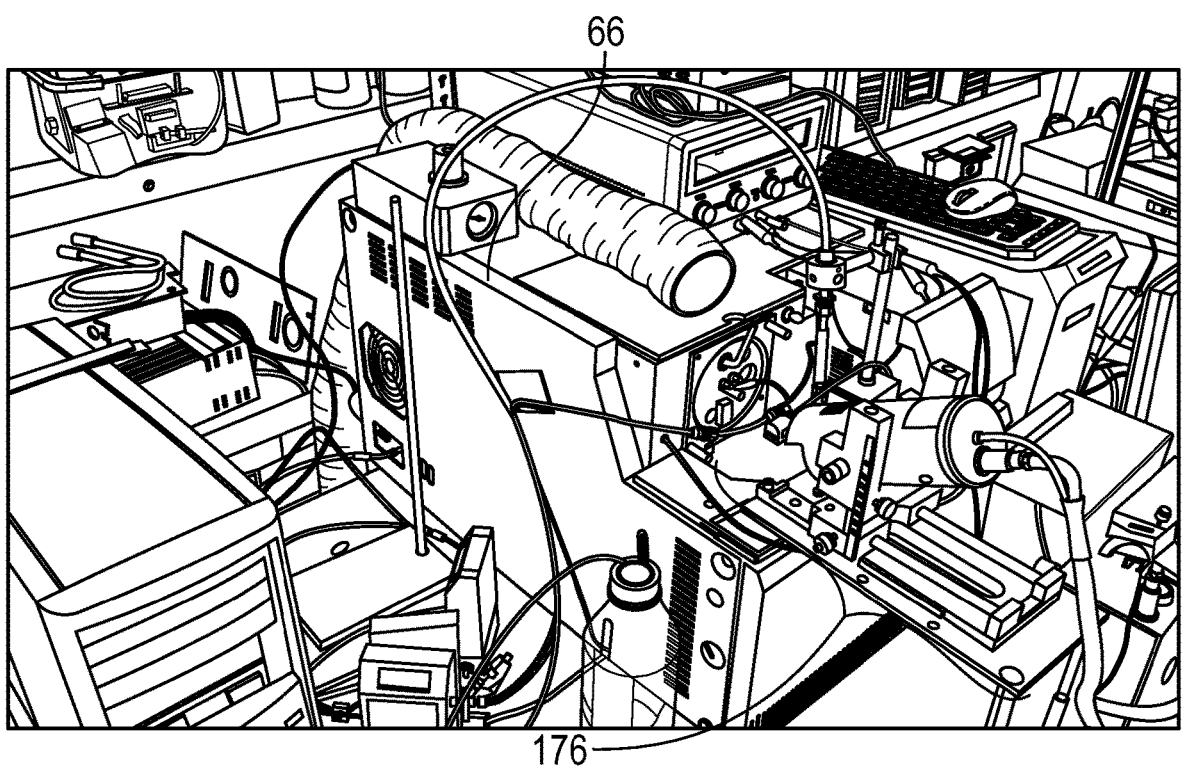
FIG. 16 is a diagram of a DART-MS apparatus modified to analyze pistachio dust or extract according to an embodiment of the present invention.

FIG. 16 shows a DART-MS apparatus modified to analyze dust or extract, with mass spectrometer 66 and DART mounting 176 positioned to accept a DART-MS substance chamber and DART-MS interface.

Figure 17:
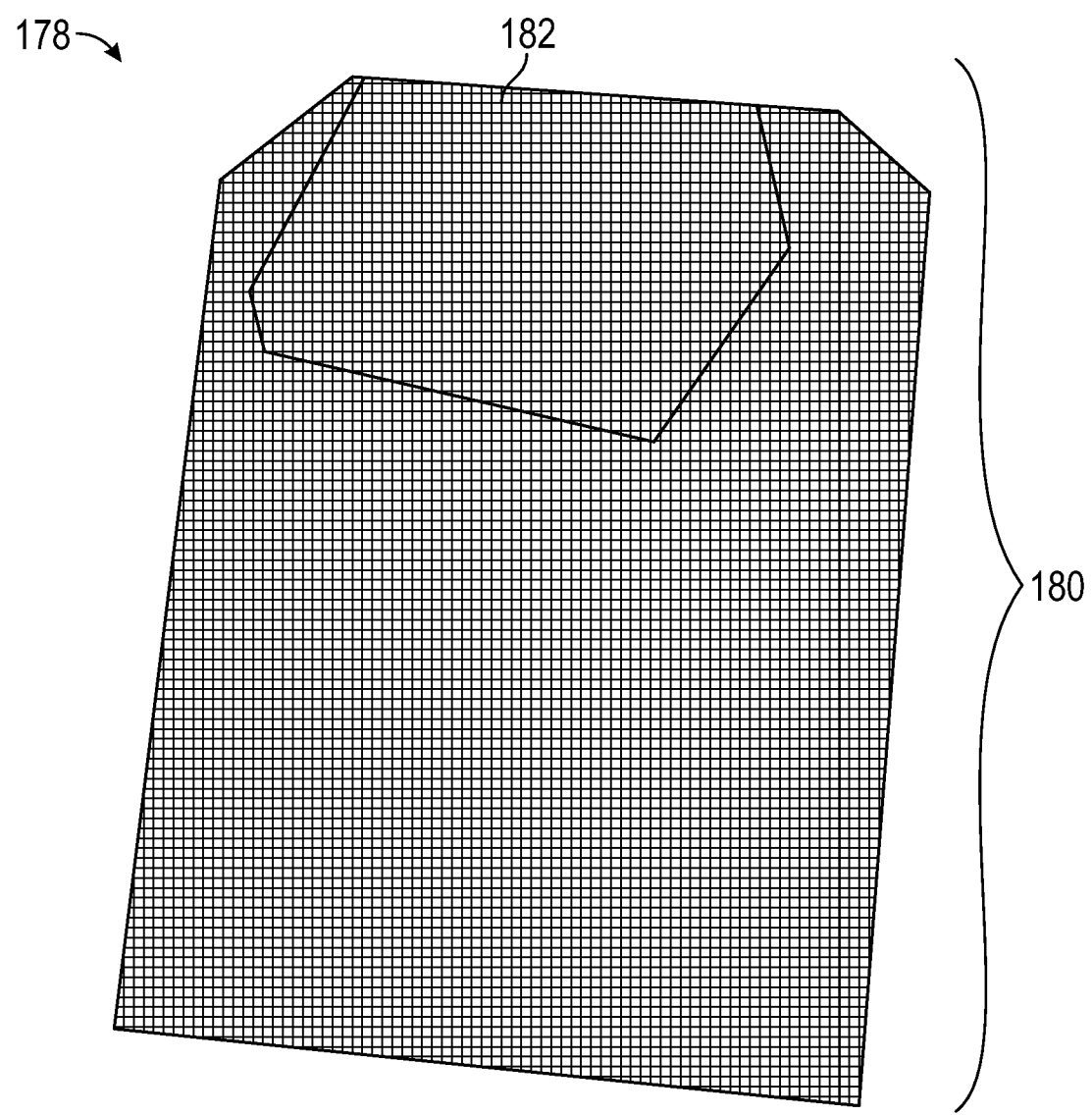
FIG. 17 is a diagram of metal mesh wetted with pistachio dust extract according to an embodiment of the present invention.

FIG. 17 shows prepared substance 178. Solvent substance was dried on stainless-steel mesh 180 to form substance extract 182.

Figure 18:
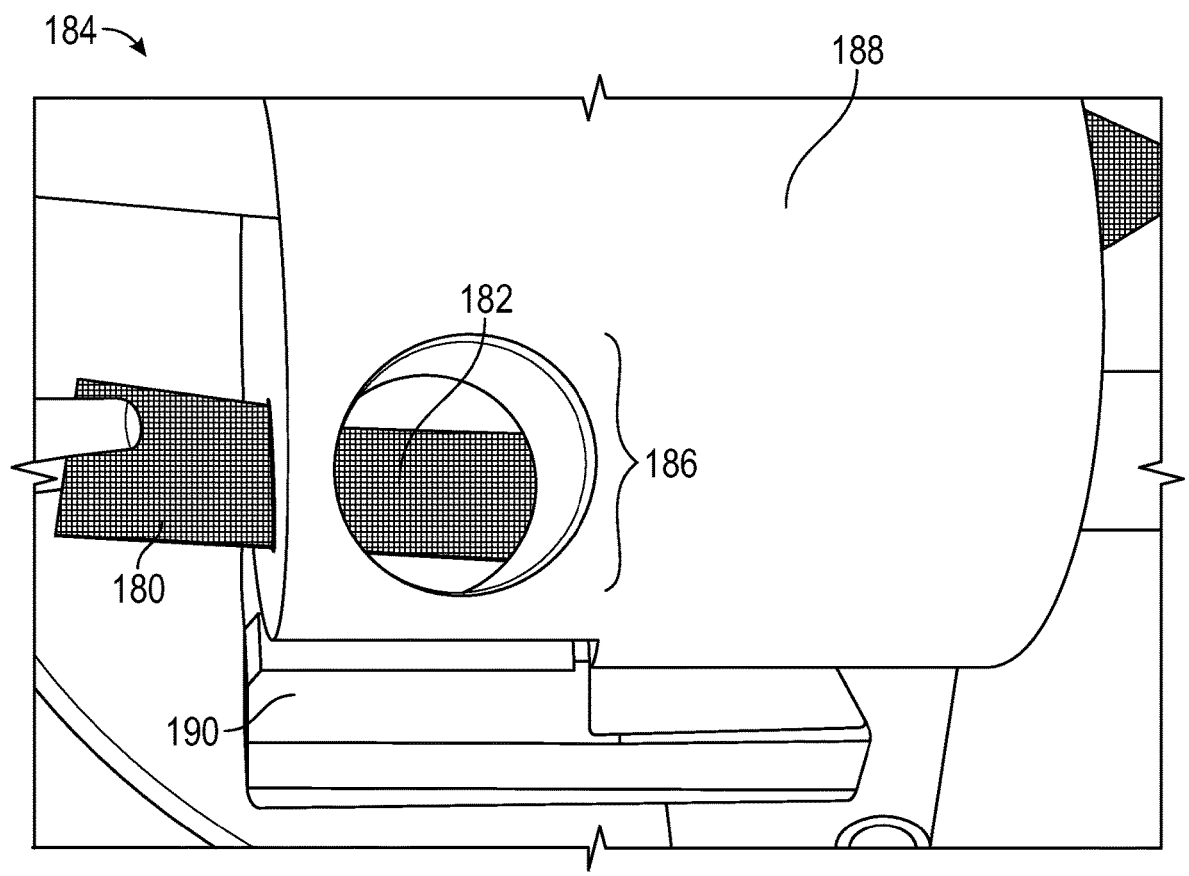
FIG. 18 is a diagram of a DART-MS substance chamber with a substance according to an embodiment of the present invention.

FIG. 18 shows DART-MS substance chamber 184 in detail. Housing 188 rests on mounting 190 and orifice 186 allows a DART ion stream to contact substance extract 182 dried on stainless-steel mesh 180.

Figure 19:
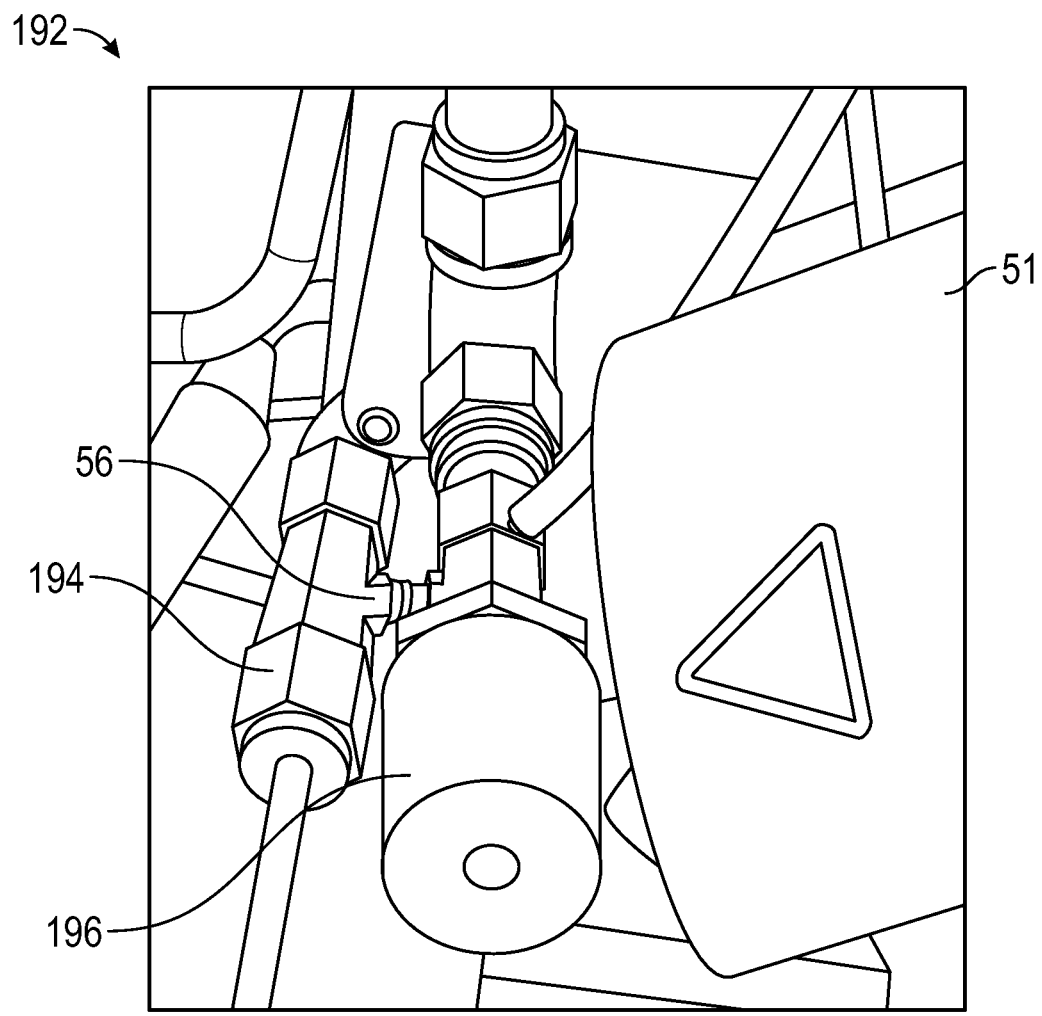
FIG. 19 is a diagram of a DART-MS interface for analyzing pistachio dust extract according to an embodiment of the present invention.

FIG. 19 shows DART-MS interface 192 with neutral excluder 56 including chamber 194 facilitating substance isolation with purified air. Neutral excluder 56 is attached to DART-MS substance chamber 196. DART 51 is positioned to direct its ion stream at a substance at least partially disposed within DART-MS substance chamber 196.

Figure 20:
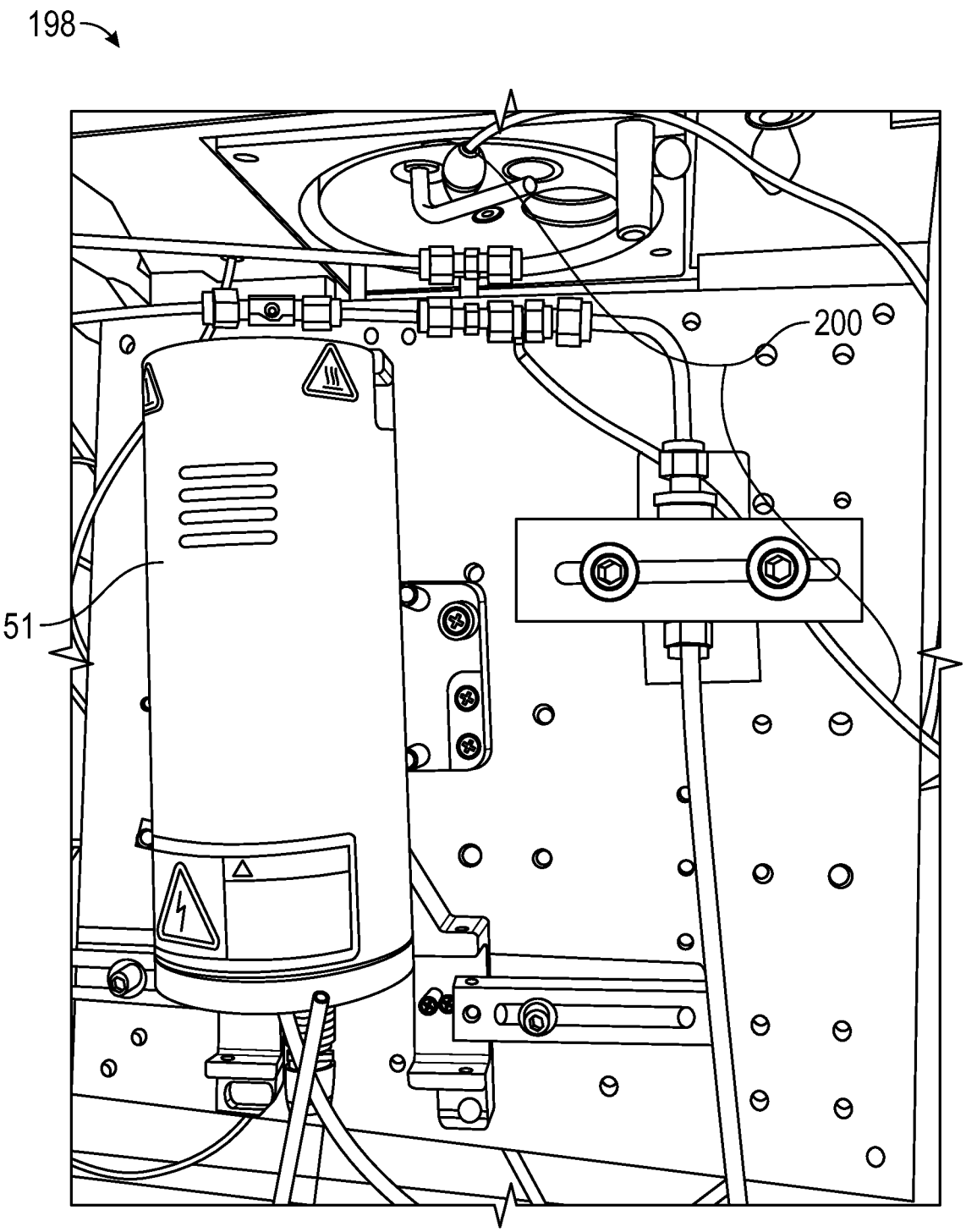
FIG. 20 is a diagram of a DART-neutral excluder-MS apparatus with a modifier after DART according to an embodiment of the present invention.

FIG. 20 shows DART-neutral excluder-MS apparatus with a modifier after DART 198. DART 51 is in communication with modifier after DART 200.

Figure 21:
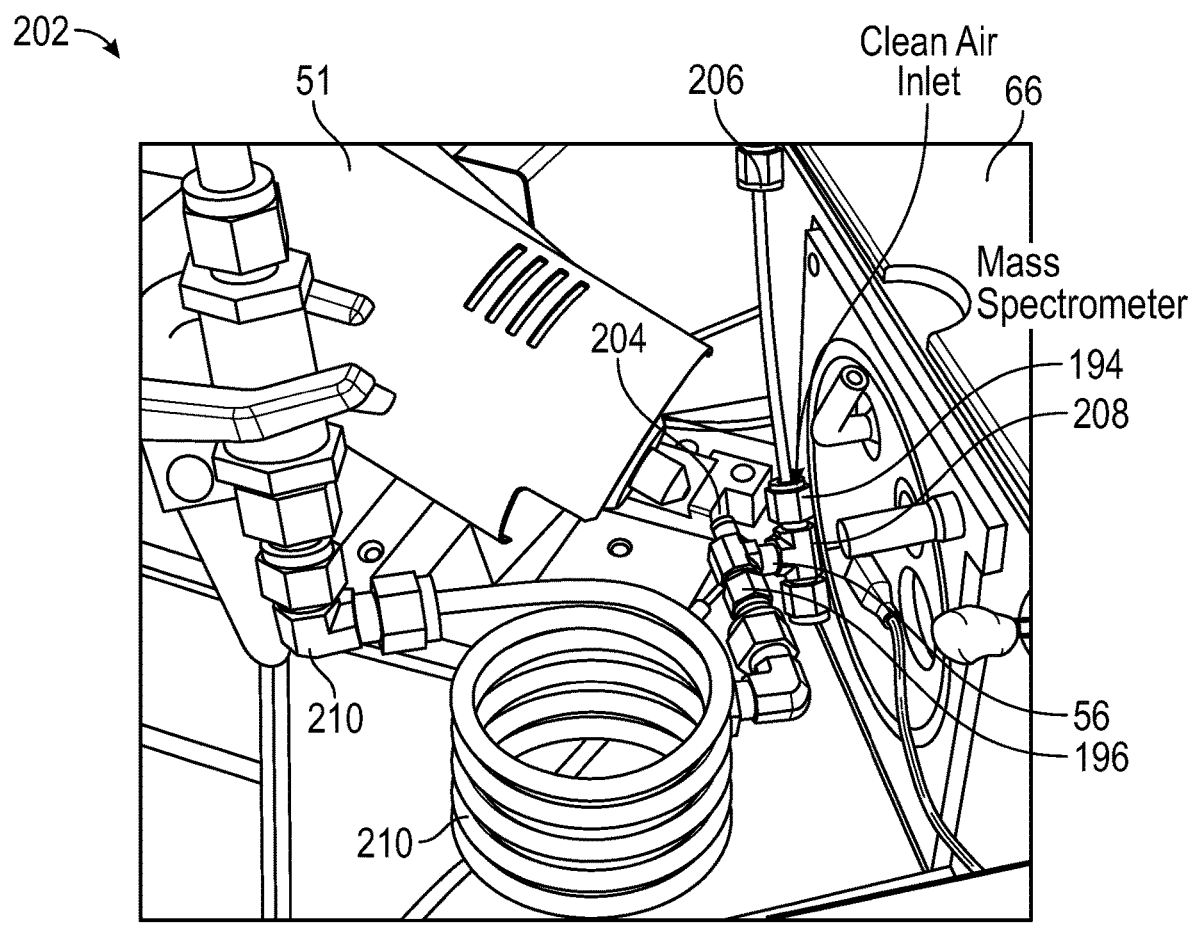
FIG. 21 is a diagram of a neutral excluder in communication with a DART and a mass spectrometer according to an embodiment of the present invention.

FIG. 21 shows DART-neutral excluder-MS apparatus 202. Neutral excluder 56 is in communication with mass spectrometer 66 via second outlet 208; suction conduit 210 via chamber 196; DART 51 via second inlet 204; and purified air conduit 206 via chamber 194.

Figure 22:
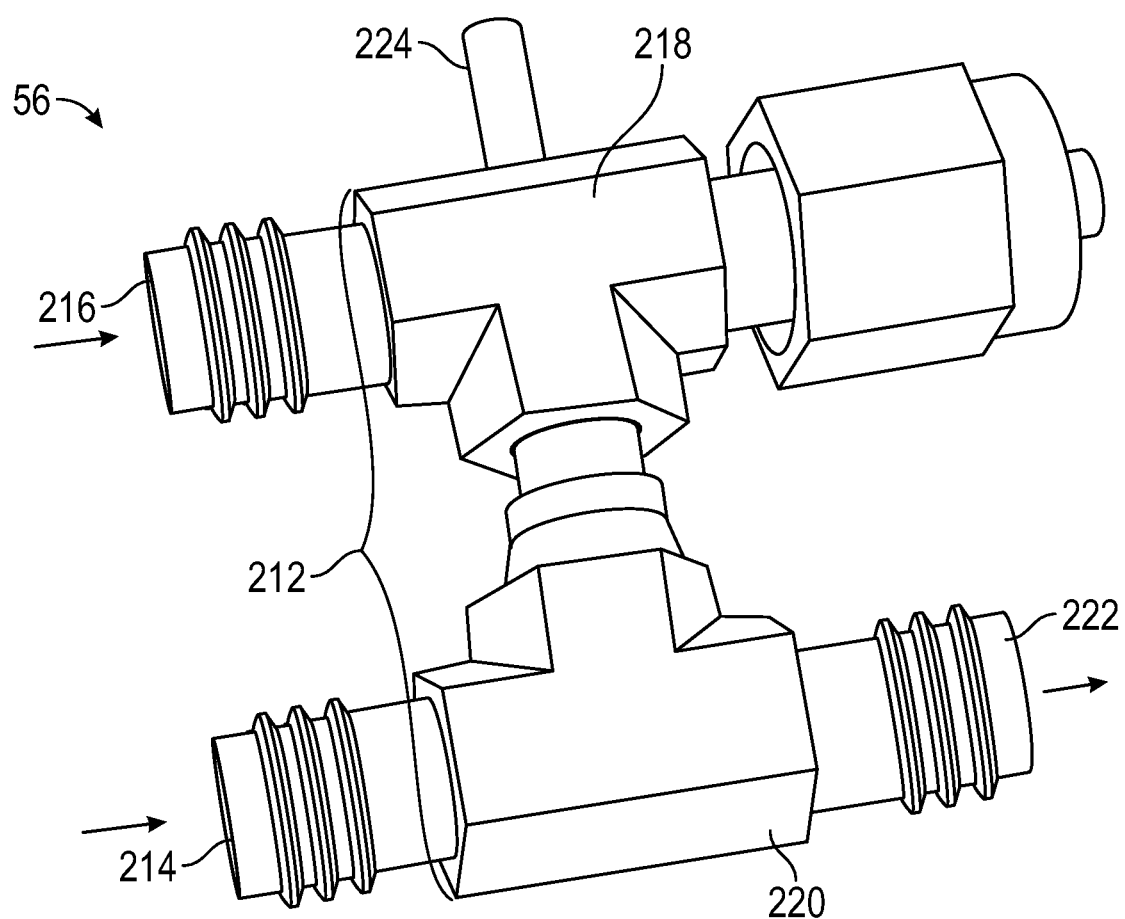
FIG. 22 is a diagram of a neutral excluder interface for a DART-MS according to an embodiment of the present invention.

FIG. 22 shows neutral excluder 56. Neutral excluder 56 comprises housing 212, which comprises first half 218 and second half 220. First half 218 comprises first inlet 216 and second outlet 224. Second half 220 comprises second inlet 214 and first outlet 222.

Figure 23:
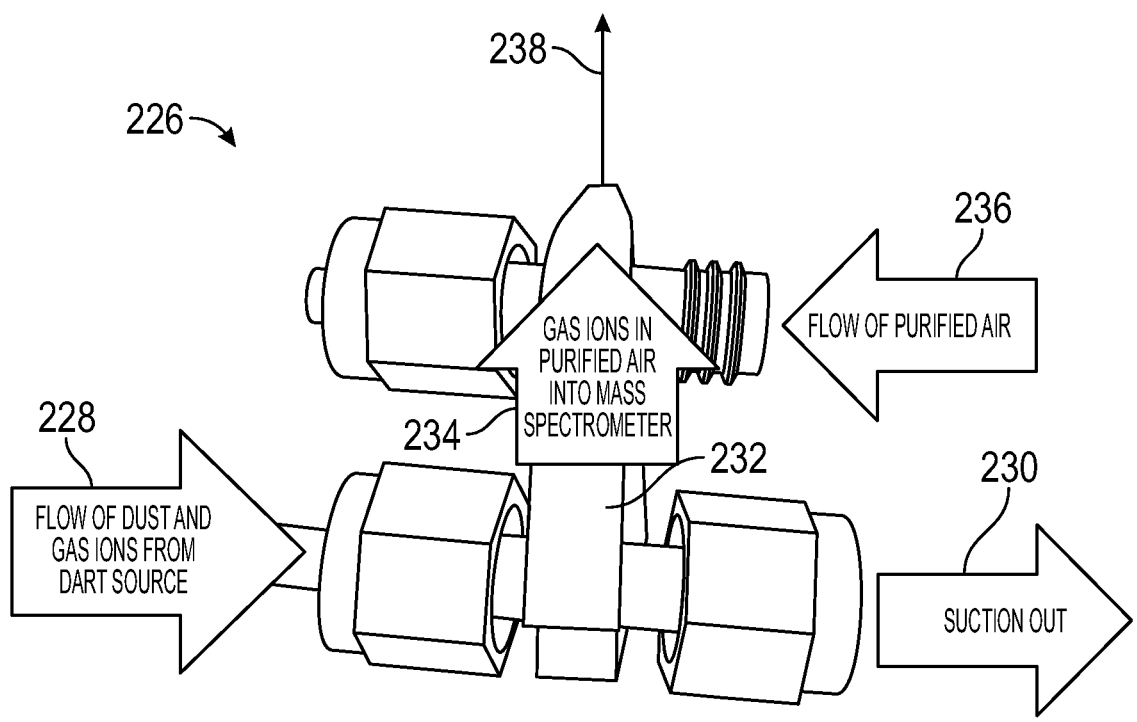
FIG. 23 is a diagram of a neutral excluder with overlaid labels showing matter flows through the neutral excluder according to an embodiment of the present invention.

FIG. 23 shows a neutral excluder with labeled flows 226. Dust and gas ion flow 228 enters the neutral excluder. A suction flow 230 is applied to draw dust and gas ion flow 228 through the neutral excluder. Flow of purified air 236 enters and combines with dust and gas ion flow 228 to form a flow of gas ion in purified air 234, which subsequently exits the neutral excluder by second outlet (tube connection) 238. Optionally, purified air 234 may be shielded by ceramic plate 232.

Figure 24:
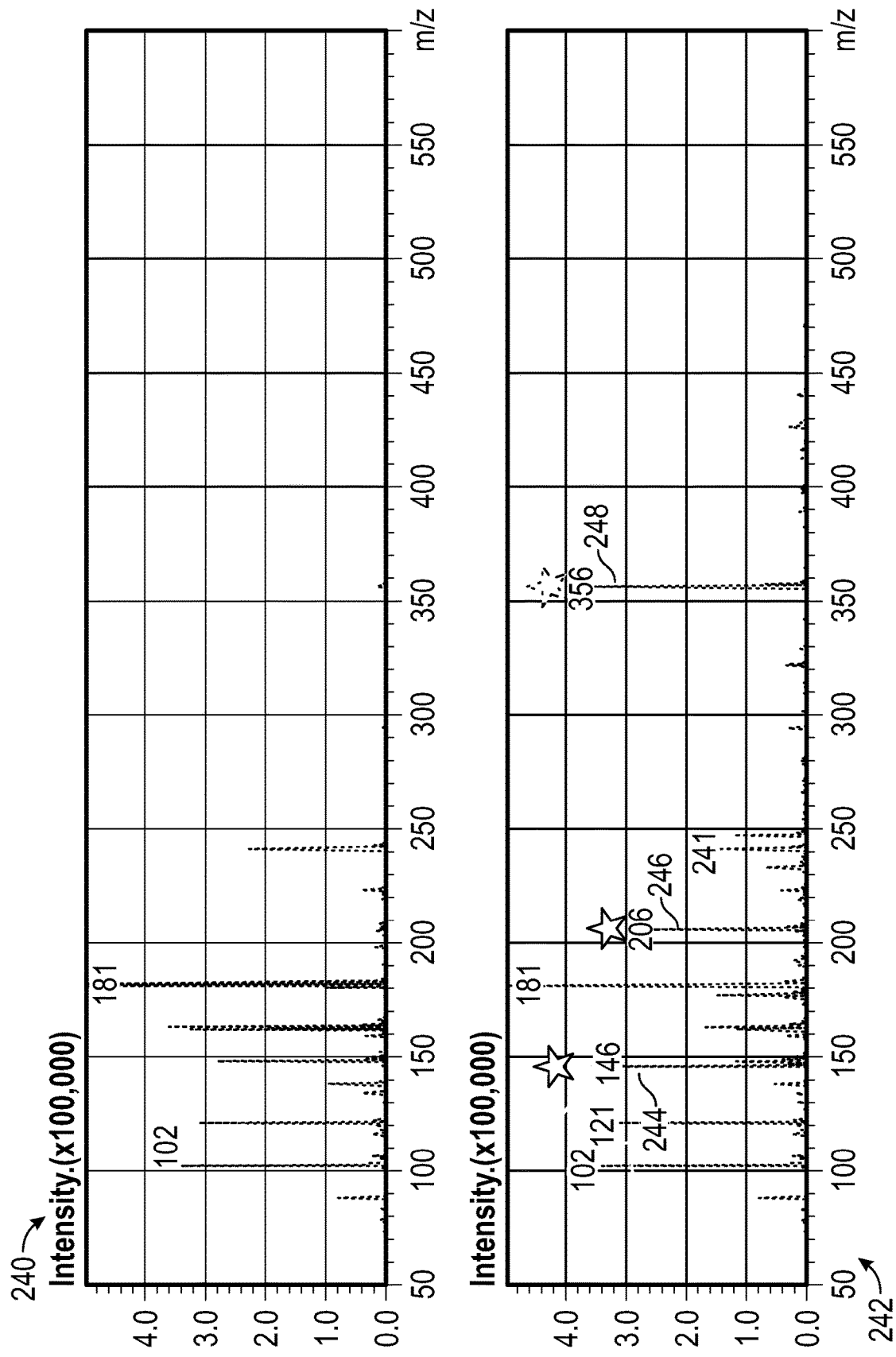
FIG. 24 is a graph showing the mass spectrometry spectra of ambient air in a pistachio processing plant and of dust samples off a surface in the pistachio processing plant according to an embodiment of the present invention.

FIG. 24 shows the mass spectrometry spectra of ambient air in a pistachio processing plant and of dust samples off a surface in the pistachio processing plant. Spectrum of ambient air 240 is compared to spectrum of dust sample 242. Peaks 244, 246, and 248 do not appear in spectrum of ambient air 240, and indicate the presence of aflatoxin.

Figure 25:
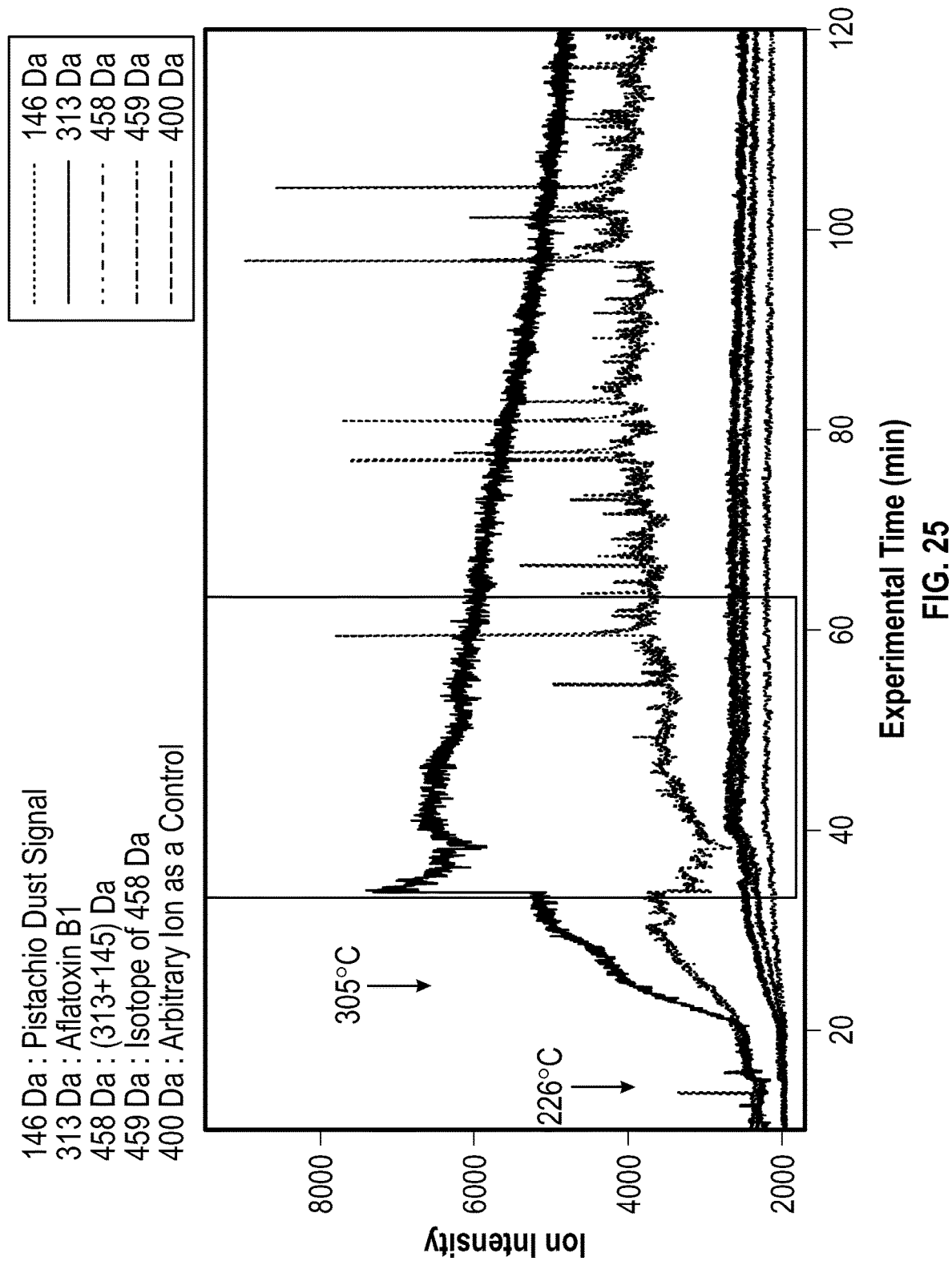
FIG. 25 is a graph showing real-time monitoring of aflatoxin B1 on pistachio flow for 120 minutes according to an embodiment of the present invention.

FIG. 25 shows real-time monitoring of aflatoxin B1 on pistachio flow for 120 minutes. Peaks for a protonated amino acid at 146 Da, aflatoxin B1 at 313 Da, and an adduct ion of aflatoxin B1 at 146 Da are shown.

Figure 26:
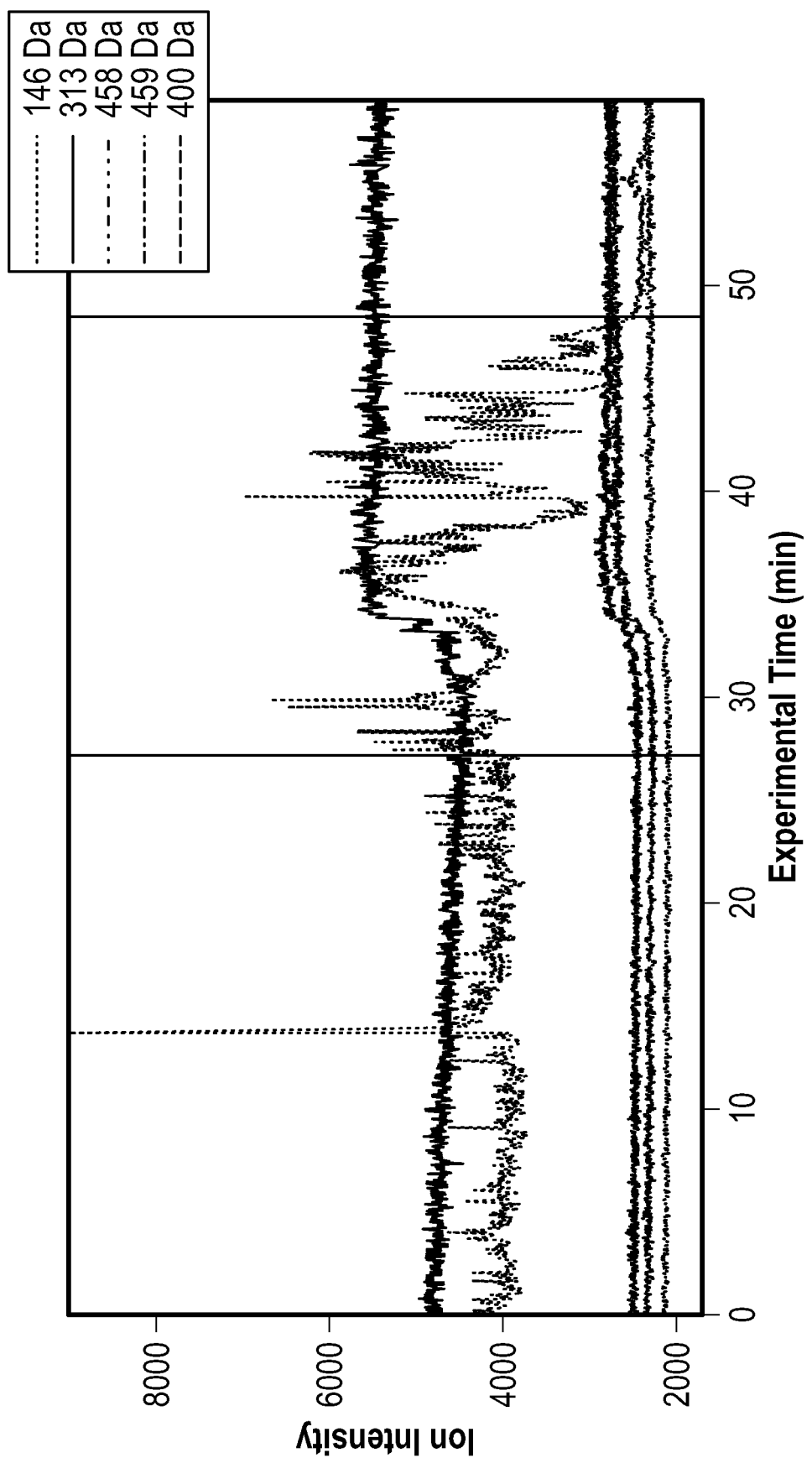
FIG. 26 is a graph showing real-time monitoring of aflatoxin B1 on pistachio flow for 50 minutes according to an embodiment of the present invention.

FIG. 26 shows real-time monitoring of aflatoxin B1 on pistachio flow for 50 minutes. Peaks for a protonated amino acid at 146 Da, aflatoxin B1 at 313 Da, and an adduct ion of aflatoxin B1 at 146 Da are shown.

Figure 27:
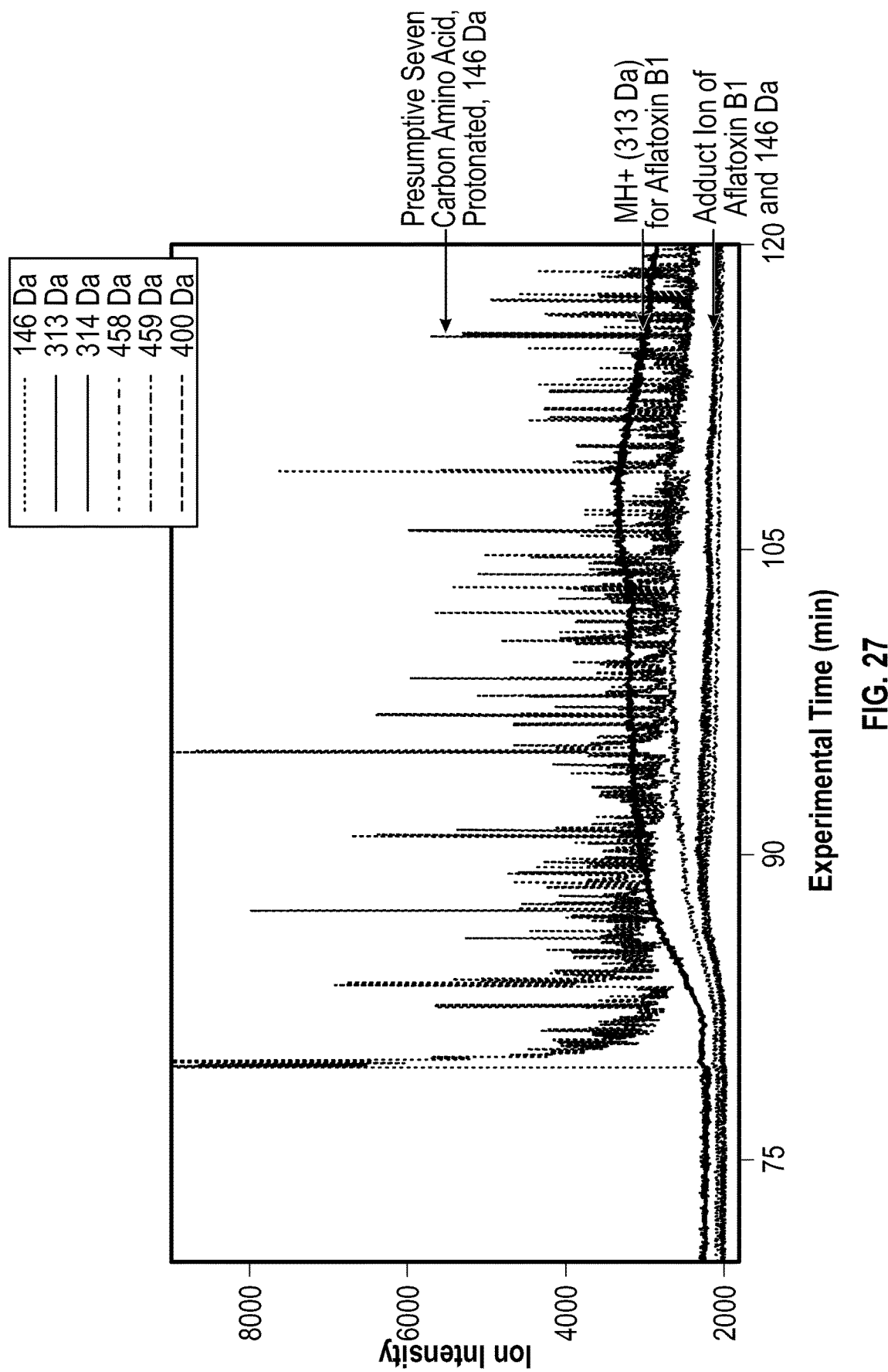
FIG. 27 is a graph showing real-time monitoring of aflatoxin B1 on pistachio flow between 75 and 120 minutes according to an embodiment of the present invention.

FIG. 27 shows real-time monitoring of aflatoxin B1 on pistachio flow between 75 and 120 minutes. Peaks for a protonated amino acid at 146 Da, aflatoxin B1 at 313 Da, and an adduct ion of aflatoxin B1 at 146 Da are shown.

Figure 28:
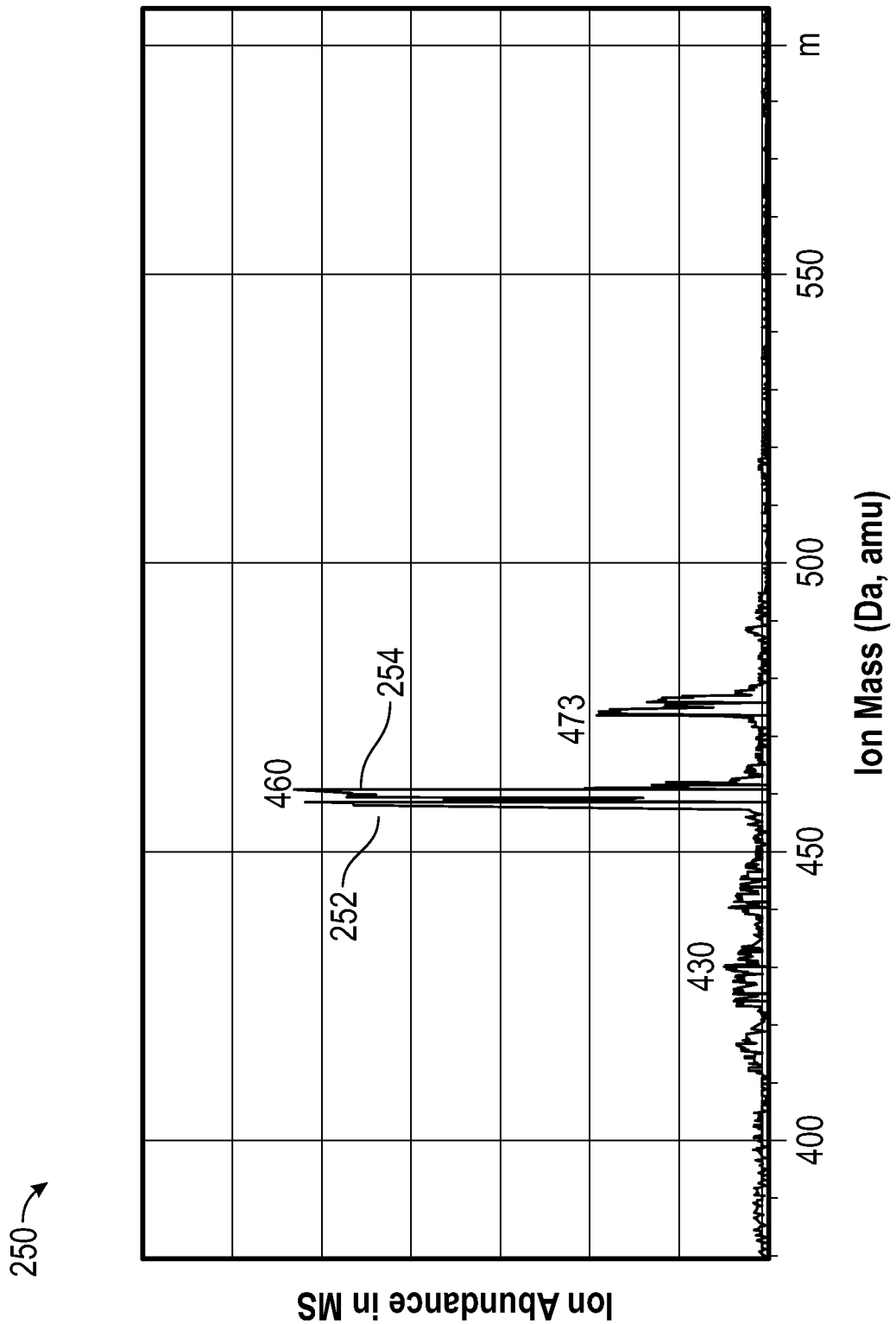
FIG. 28 is a graph showing the results from DART-MS analysis of various aflatoxins and associated adduct ions according to an embodiment of the present invention.

FIG. 28 shows the results from DART-MS analysis of various aflatoxins and associated adduct ions. Aflatoxin ions are adducted according to the formula $MH^+ + B \rightarrow MH^+B$. Graph 250 shows an aflatoxin+extract substance with ion-adducted aflatoxins B1 and B2 at peaks 252 and 254, respectively.

Figure 29:
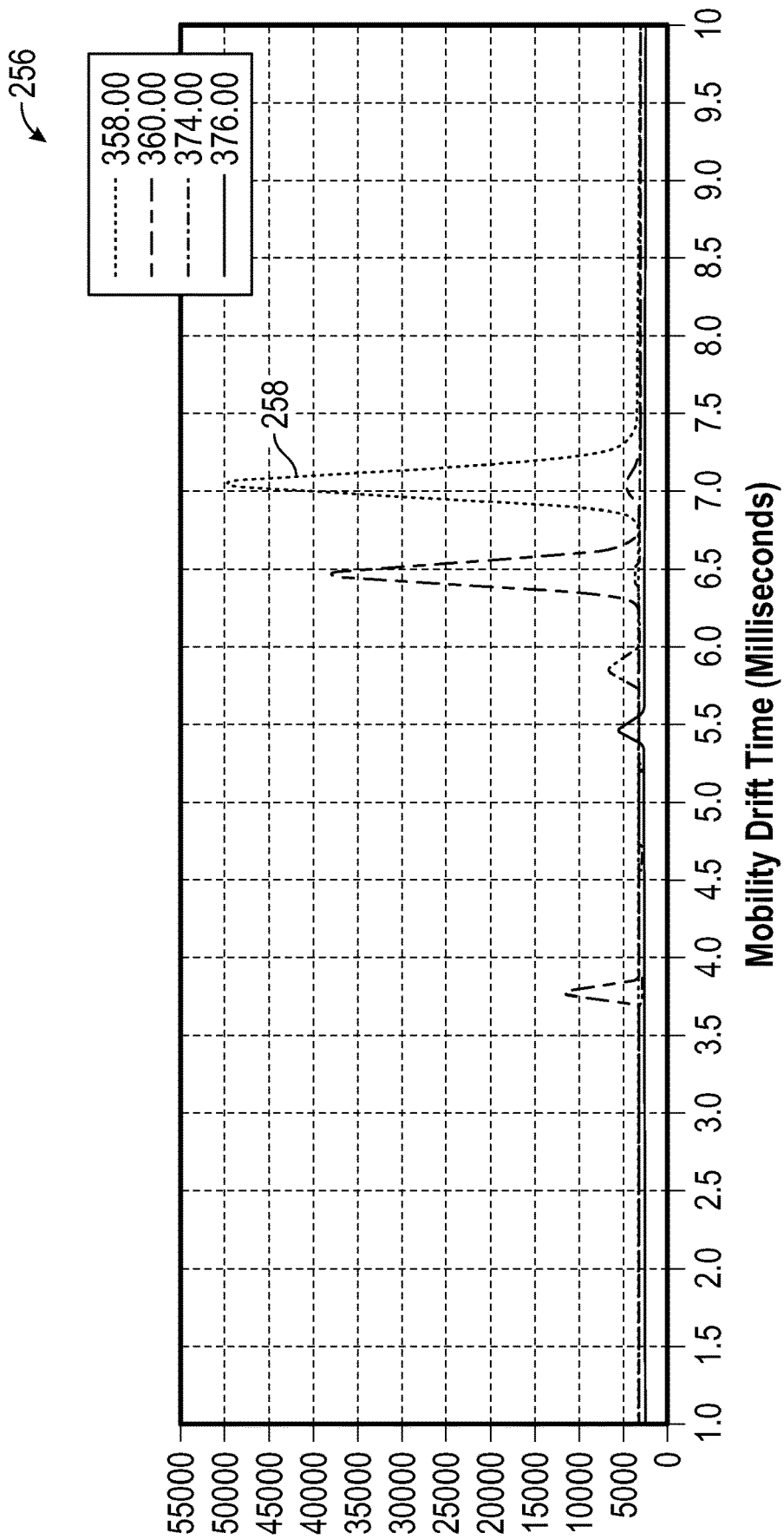
FIG. 29 is an LC/MS chromatograph showing aflatoxins in dust substances with a diameter greater than about 250 μm according to an embodiment of the present invention.

FIG. 29 shows LC/MS chromatograph 256 identifying aflatoxins in dust substances with a diameter greater than about 250 μm at peak 258.

Figure 30:
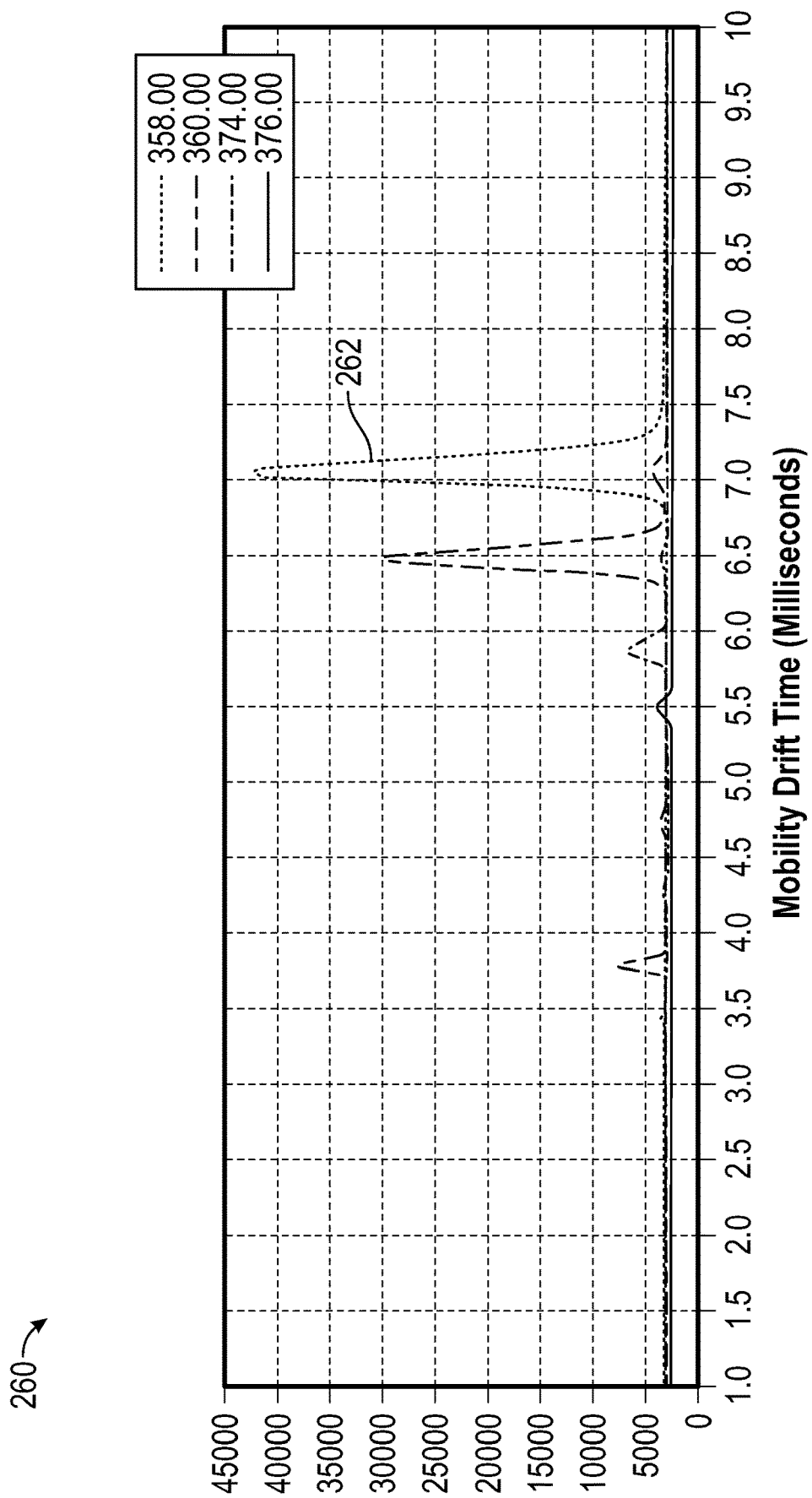
FIG. 30 is an LC/MS chromatograph showing aflatoxins in dust substances with diameters between about 125 μm to about 250 μm according to an embodiment of the present invention.

FIG. 30 shows LC/MS chromatograph 260 identifying aflatoxins in dust substances with diameters between about 125 μm to about 250 μm at peak 262.

Figure 31:
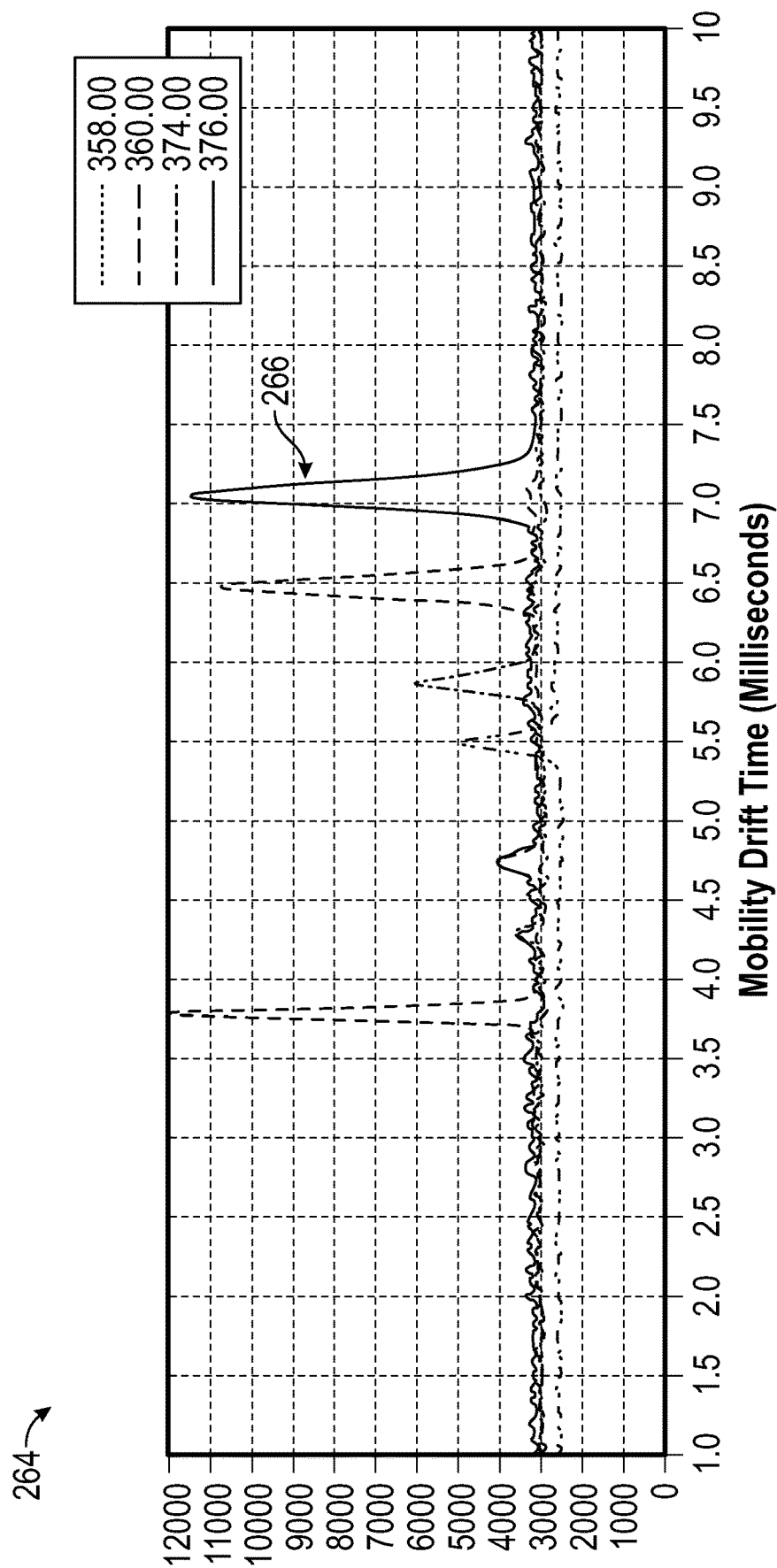
FIG. 31 is an LC/MS chromatograph showing aflatoxins in dust substances with diameters less than about 125 μm according to an embodiment of the present invention.

FIG. 31 shows LC/MS chromatograph 264 identifying aflatoxins in dust substances with diameters less than about 125 μm at peak 266.

FIG. 32 shows example results from an analysis of pistachio dust. The table shows that pistachio dust particles less than 125 microns in diameter have the greater amount of aflatoxin B1.

Figure 33A:
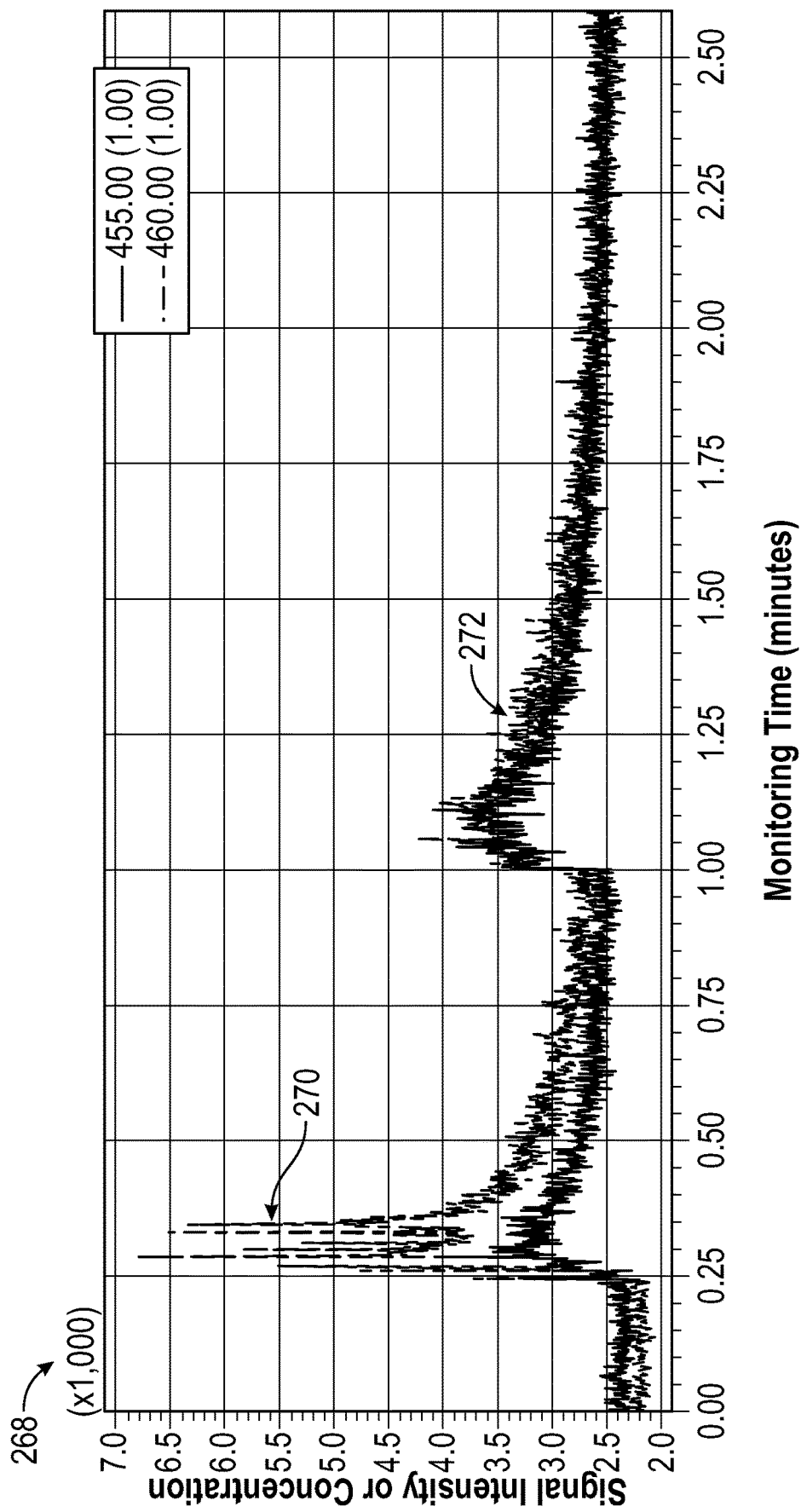
FIGS. 33A, FIG. 33B, and FIG. 33C are graphs showing direct dust sampling from room air, with DART at 450° C. and no heater according to an embodiment of the present invention.
Figure 33B:
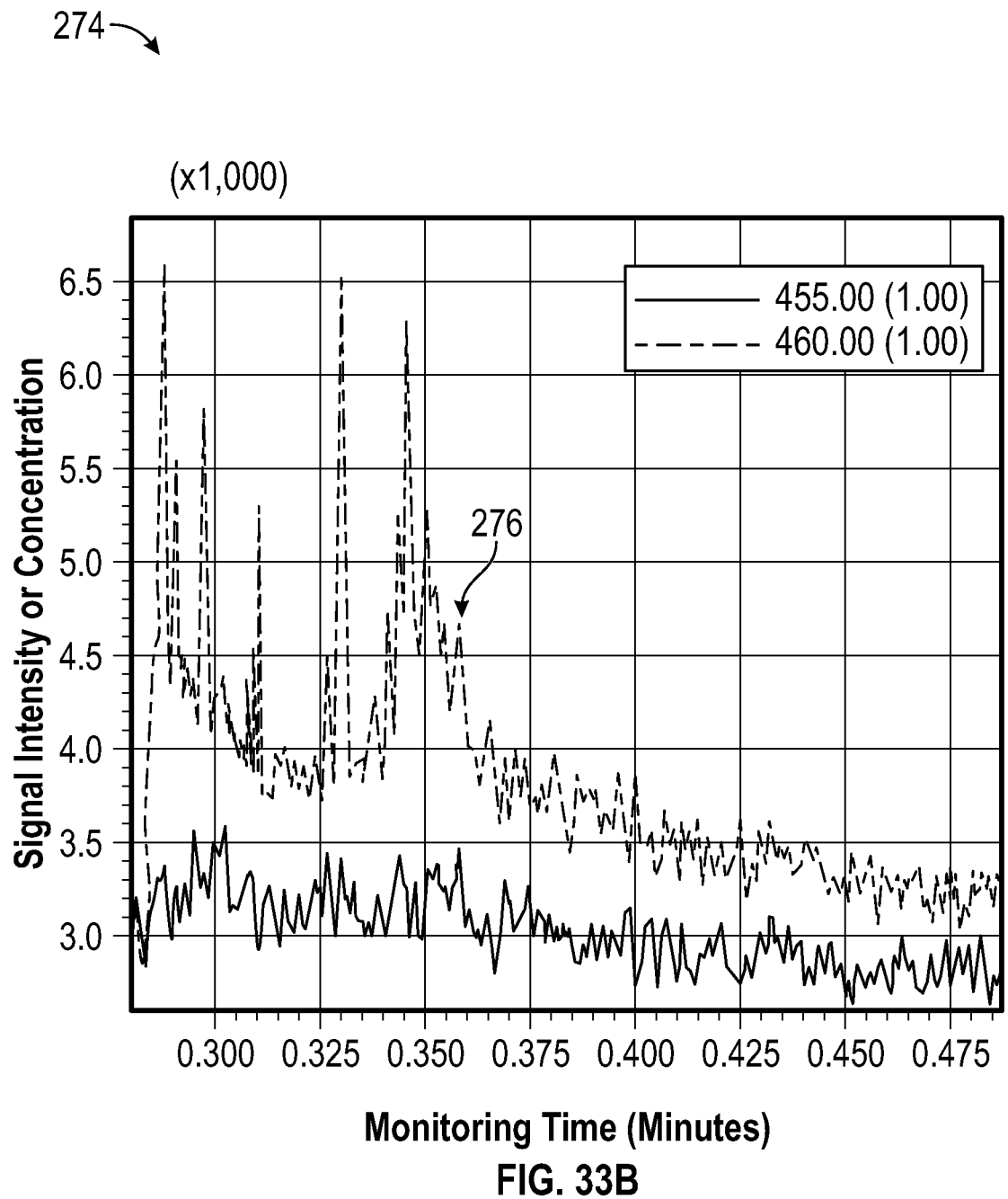
Figure 33C:
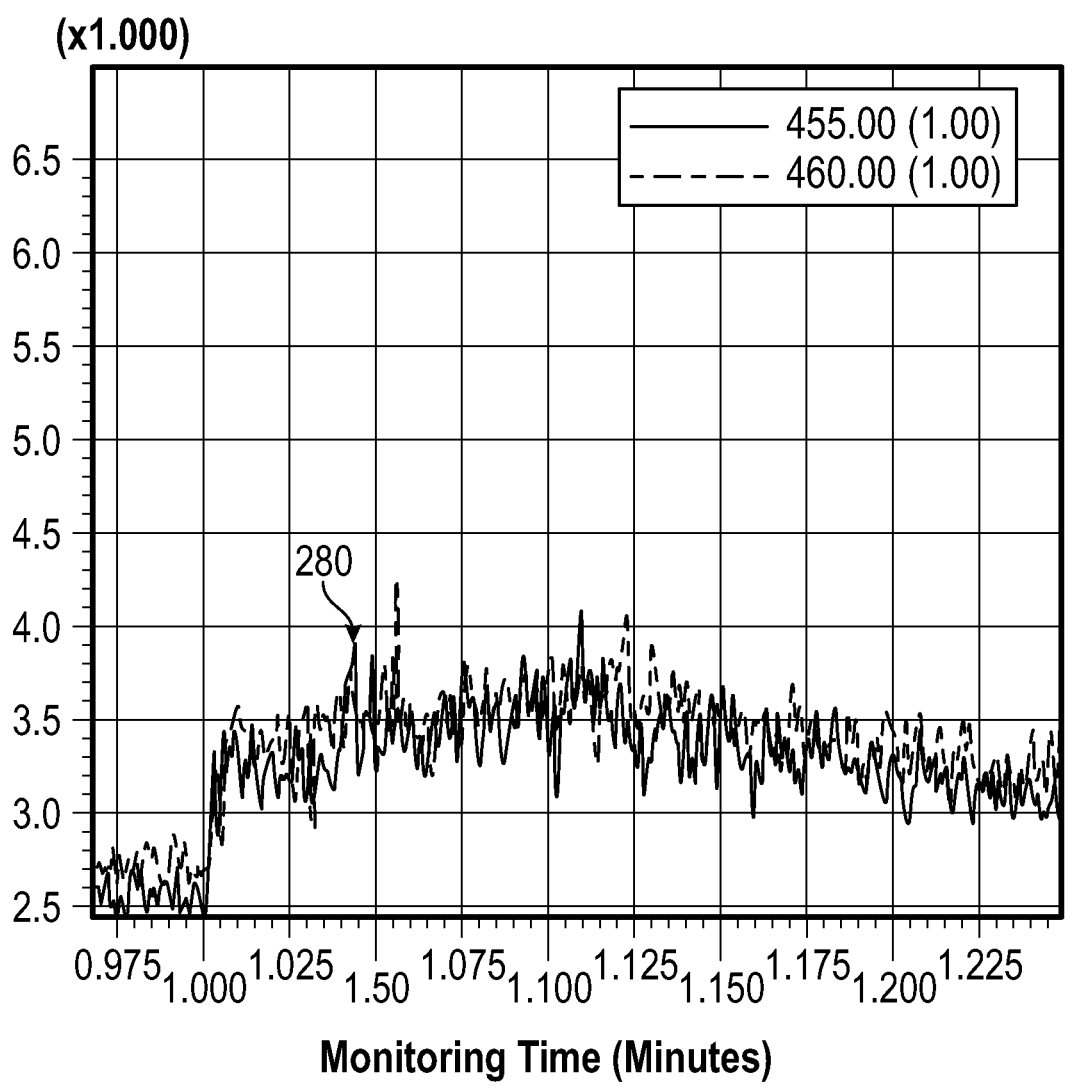

FIGS. 33A, FIG. 33B, and FIG. 33C show graphs 268, 274, and 278 of direct dust sampling from room air, with DART at 450° C. and no heater. Monitoring dust with known aflatoxin is shown by peaks 270 and 276 and monitoring dust without aflatoxin is shown by peak 272 and 280.

Figure 34:
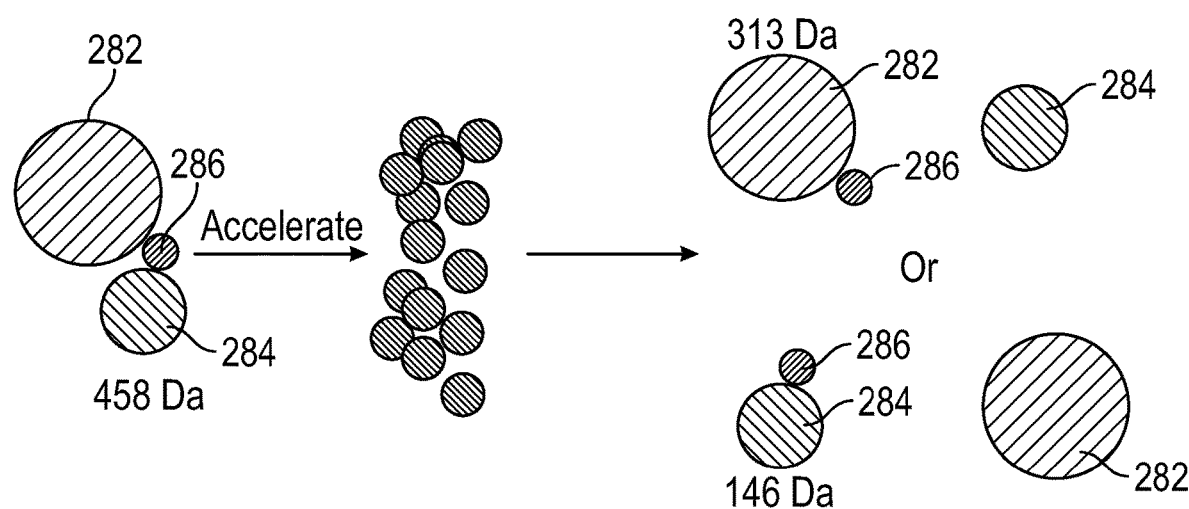
FIG. 34 is a diagram showing the dissociation of aflatoxin, an adducted ion, and a proton by mass spectrometry according to an embodiment of the present invention.

FIG. 34 shows the dissociation of aflatoxin, an adducted ion, and a proton by mass spectrometry. Aflatoxin B1 282, adducted ion 284, and proton 286 are associated before entering a mass spectrometer. Aflatoxin B1 282, adducted ion 284, and proton 286 can dissociate into aflatoxin B1 282 and proton 286, and adducted ion 284. Alternatively, aflatoxin B1 282, adducted ion 284, and proton 286 can dissociate into aflatoxin 282, and adducted ion 284 and proton 286.

Figure 35:
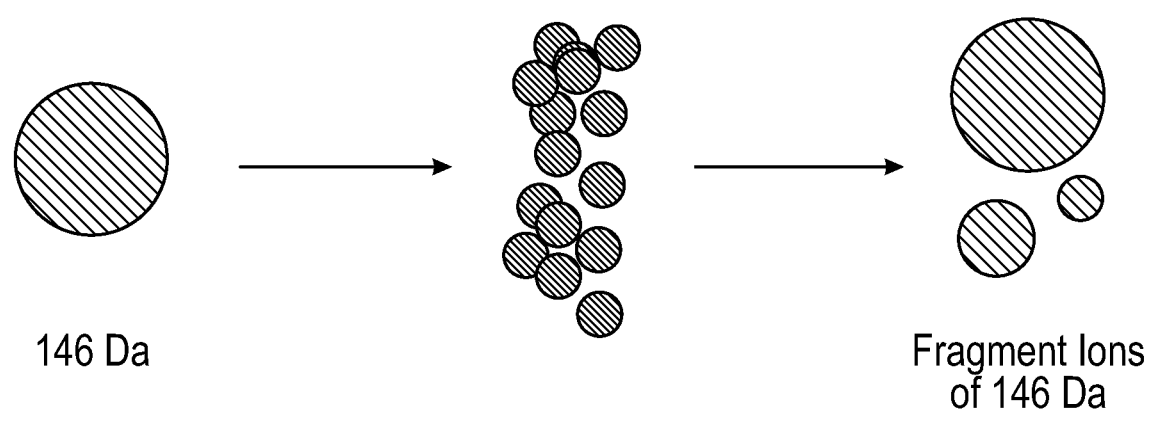
FIG. 35 is a diagram showing the dissociation of an adducted ion according to an embodiment of the present invention.

FIG. 35 shows the dissociation of an adducted ion. The adducted ion can dissociate into fragment ions.

Figure 36A:
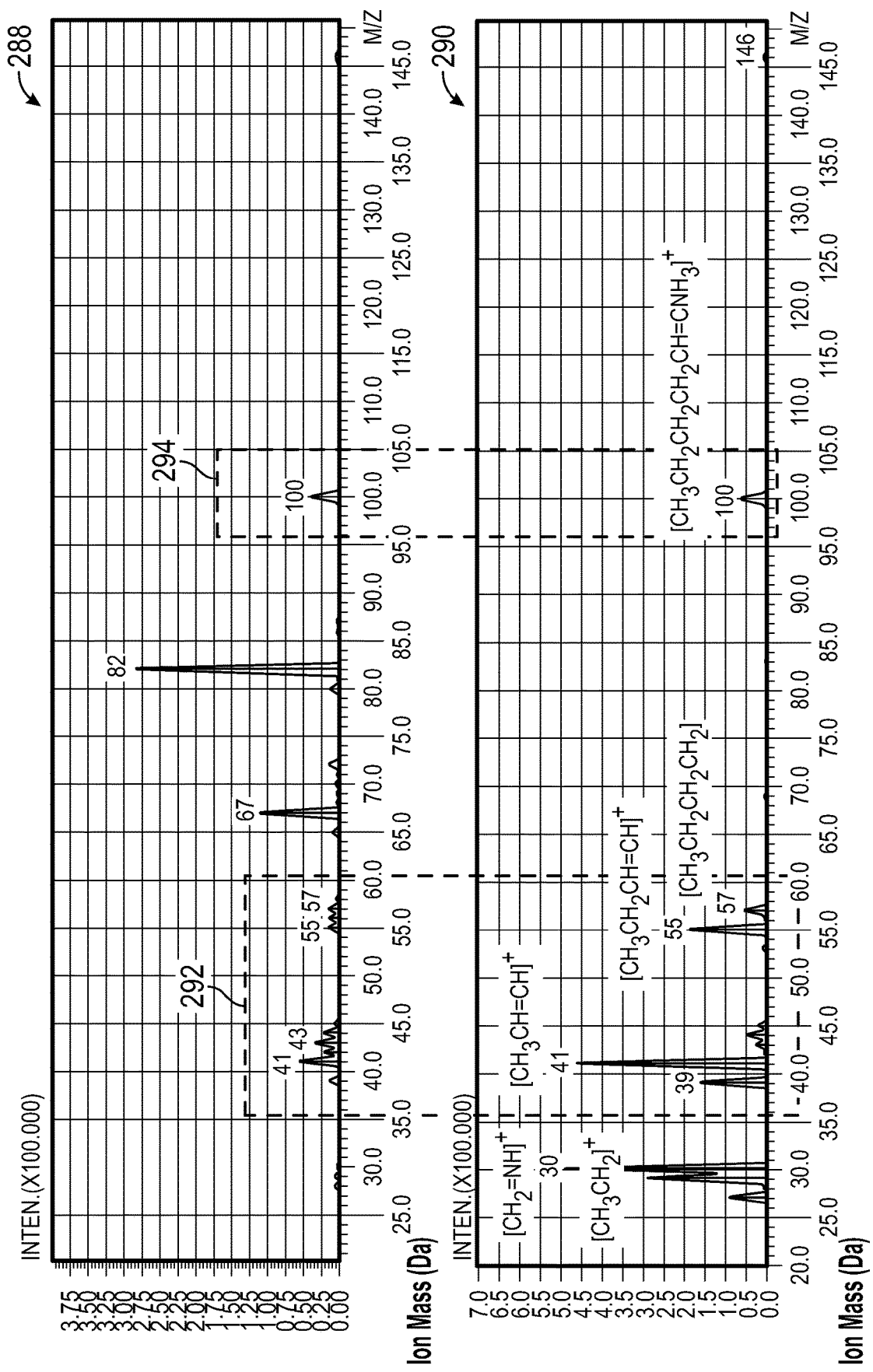
FIG. 36A and FIG. 36B are graphs showing the mass spectrometry spectra of an adducted ion according to an embodiment of the present invention.
Figure 36B:
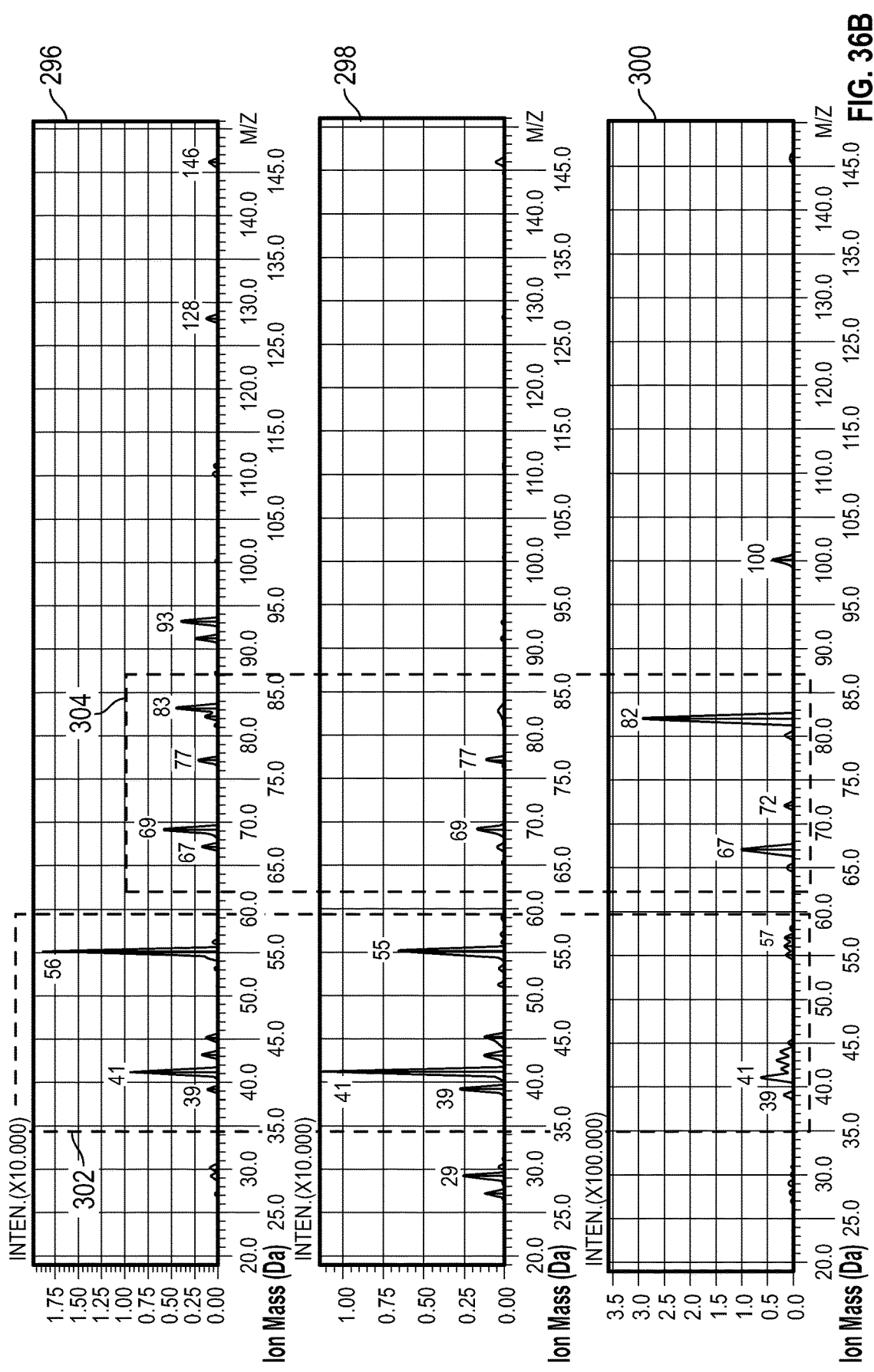

FIG. 36A shows showing the mass spectrometry spectra of an adducted ion. Spectrum of fragmentation of unknown ion (146 Da) at 38V 288 and spectrum of fragmentation of protonated 2-amino heptanoic acid (146 Da) at 38V 290 show similar peaks 292 and 294. FIG. 36B shows the mass spectrometry spectra of an adducted ion. Spectrum of 3-aminoheptnaoic acid at −38V 296; spectrum of 7-aminoheptanoic acid at −38V 298; and spectrum of dust −38V 300 show similar peaks 302 and 304. The identity of the adducted ion may be 2-aminoheptanoic acid, 3-aminoheptanoic acid, 7-aminoheptanoic acid, or a combination thereof.

The apparatus may comprise a neutral excluder. The neutral excluder may comprise: a first housing having a first end and second end and forming an outer cavity space; a second housing with a first end and second end, disposed within the outer cavity space, and forming a middle cavity space; a third housing with a first end and second end, disposed within the middle cavity, and forming an inner cavity; a first inlet for receiving ionized matter; and a second inlet for receiving gas. The outer cavity may receive an ionized gas. The middle cavity may receive a gas. The inner cavity may receive a gas comprising e.g., a purified ionized gas. The first end of the first housing may have an orifice. Waste gas may exit through the orifice. The second end of the first housing may be sealed. The first end of the second housing may be in communication with the outer cavity. The second end of the second housing may be sealed. The first end of the third housing may be in communication with the outer cavity. The second end of the third housing may be in communication with a mass spectrometer. The neutral excluder may be in communication with a mass spectrometer, a DART, an after-DART modifier, a particular filter, a vessel, or a combination thereof. The apparatus may further comprise an alcohol. The alcohol may comprise, but not be limited to, propanol, alcohol or other vapor modifiers including, volatile organic compounds. The propanol may comprise, but not be limited to, 2-propanol. The apparatus may further comprise a suction pump. The apparatus may also comprise a gas. The gas may be purified and may comprise, but not be limited to, air, nitrogen, helium or a combination thereof. The apparatus may further comprise a substance. Gas may be flowed through the neutral excluder and may function to purify the substance. The substance may be organic or not organic. The substance may comprise agricultural products including nuts and/or other agricultural products, including those described herein. The nuts may comprise, but not be limited to, pistachios. The substance may comprise agricultural dust including, but not limited to, pistachio dust. The DART may be a pulsed DART or a continuous flow DART.

The apparatus may analyze a substance. The substance may be organic or not organic. The substance may comprise agricultural products including nuts and/or agricultural products as described above. The nuts may comprise pistachios. The substance may comprise agricultural dust including, but not limited to, pistachio dust. The substances may comprise particle sizes of at least about 5 μm, about 5 μm to about 500 μm, about 25 μm to about 450 μm, about 50 μm to about 400 μm, about 75 μm to about 350 μm, about 100 μm to about 300 μm, about 125 μm to about 250 μm, about 150 μm to about 225 μm, about 175 μm to about 200 μm, or about 500 μm.

The apparatus may comprise a separator. The separator may comprise a cyclone separator, filter, centrifuge, or a combination thereof.

The neutral excluder may comprise an insulator. The insulator may be a layer of material at least partially disposed along the housing and/or channel of the neutral excluder. The insulator may comprise a ceramic material, air, an inert gas, a mesh, a foam, other porous material, or a combination thereof.

The apparatus and/or method of the present invention may be used to analyze a substance. The substance may comprise organic matter or not organic matter. The substance may be a solid and/or solid particulate, e.g., dust. The substance may comprise agricultural products including but not limited to nuts and/or grains. The nuts may comprise, but not be limited to, pistachios. The substance may comprise agricultural dust including, but not limited to, dust from agricultural products and/or nuts. The nuts may comprise, but not be limited to, pistachios, almonds, pecans, walnuts, cashews, peanuts, other nut products, or a combination thereof. The agricultural products may comprise, but not be limited to, corn, soybean, wheat, grains, sorghum, rice, chili, coffee, grapes, cocoa, cacao, legumes, chocolate, potatoes, tuberous vegetables, cereal, figs, animal feed, other agricultural products, or a combination thereof. The tuberous vegetables may comprise carrots, radishes, cassava, artichoke, jicama, sweet potato, yam, taro, water chestnut, turmeric, *ginseng*, lotus root, ginger, groundnut, turnips, parsley root, or a combination thereof. Animal feed may comprise alfalfa, barley, oats, cereals, or a combination thereof. The substance may also comprise a toxin, contaminant, explosive agent, pathogen, amino acid, or a combination thereof.

DART ionization, in combination with mass spectrometry, may be used to characterize particulate matter suspended in a flow of gas for the direct determination of aflatoxins without liquid extraction or handling by humans. This invention allows for continuous and/or live detection of aflatoxins in pistachios and other nut and agricultural products.

Isopropanol vapors may be introduced into the substance flow to suppress the mass spectral response ions from large numbers of constituents in the substance dust that produce ions of relatively moderate intensity and which complicate the appearance of the mass spectral response. The addition of vapors of isopropanol at least partially eliminates ions between 250 and 600 Da, making a clean baseline for response to aflatoxin adducts.

A DART-neutral excluder-MS particulate matter detection limit may be at least 20 ppb. The limits of intensity detection may be reduced by a natural abundance of a substance also with ion mass of 458 Da. An ion at 457 Da is also observed in a substance. In instances when aflatoxin is not present in the measurement, the intensity for 457 Da greater than 458 Da. This inequality may be reversed in the presence of aflatoxin such that the 457 Da ion abundance is less than the 458 Da ion abundance.

An additive to replace the 146 Da ion mass may be used. The substance responsible for the 146 Da ion (and thus the adduct 458 Da ion for aflatoxin B1) may be a constituent in the dust and may have a strong proton affinity or favorable ionization properties with DART. Efforts to suppress the formation of this ion have been unsuccessful; however, substitution or replacement might be useful since there is a substance that does produce a 458 Da ion, which is usually checked against 457 Da for detecting aflatoxins. A substance may be used to "tailor" and adduct to a specific mass of choice, for example to locate the adduct ion in a mass region of ultra-low abundance of signal. Detection limits and false positives may be significantly improved with use of the additive.

An alternative gas to isopropanol may be used in the DART-neutral excluder-MS. The addition of vapors of isopropanol (rubbing alcohol) to the DART-neutral excluder-MS may improve the measurement of dust for aflatoxins by suppressing the ionization of naturally abundant constituents in the dust. This simplifies the analytical signal (i.e., mass spectra) and this improves interpretations of the mass spectra. Other possible vapor may include, but are not limited to, other volatile organic compounds.

The apparatus may be operated under different flow rates. Ionic matter may be flowed into the mass spectrometer at a rate of at least about 0.1 L/min, about 0.1 L/min to about 1.0 L/min, about 0.2 L/min to about 0.9 L/min, about 0.3 L/min to about 0.8 L/min, about 0.4 L/min to about 0.7 L/min, about 0.5 L/min to about 0.6 L/min, or about 1.0 L/min. The substance may be flowed at a rate of at least about 0.2 L/min, about 0.2 L/min to about 2.0 L/min, about 0.4 L/min to about 1.8 L/min, about 0.6 L/min to about 1.6 L/min, about 0.8 L/min to about 1.4 L/min, about 1.0 L/min to about 1.2 L/min, or about 2.0 L/min into the DART energy stream. The DART ion/energy stream may be flowed at rate of at least about 0.3 L/min, about 0.3 L/min to about 3.0 L/min, about 0.6 L/min to about 2.7 L/min, about 0.9 L/min to about 2.4 L/min, about 1.2 L/min to about 2.1 L/min, about 1.5 L/min to about 1.8 L/min, or about 3.0 L/min. The gas phase substance may be passed through the neutral excluder. The substance may comprise a mixture of ionic and nonionic matter. The matter may be particulate matter, dust, gaseous matter, or a combination thereof. The substance may be flowed through the neutral excluder to purify the substance by separating the ionic matter from the nonionic matter. The apparatus may further comprise a suction pump. The suction pump may cause a flow at a rate of at least about 0.1 L/min, about 0.1 L/min to about 5.0 L/min, about 0.5 L/min to about 4.5 L/min, about 1.0 L/min to about 4.0 L/min, about 1.5 L/min to about 3.5 L/min, about 2.0 L/min to about 3.0 L/min, or about 5 L/min. Purified air may be flowed into the neutral excluder at a rate of at least about 0.1 L/min, about 0.1 L/min to about 1.9 L/min, about 0.3 L/min to about 1.7 L/min, about 0.5 L/min to about 1.5 L/min, about 0.7 L/min to about 1.3 L/min, about 0.7 L/min to about 1.1 L/min, or about 1.9 L/min.

Ions generated by DART treatment of particulates in a substance flow may pass through the neutral excluder and into the interface of a mass spectrometer, the reaction region of an ion mobility spectrometer, into an ion mobility spectrometer/mass spectrometer, or a combination thereof. The ions generated by DART may be subjected to mass analysis, mobility analysis, or combination thereof. Mass analysis may be performed by mobility or mass spectrometer, including tandem mass spectrometers.

The apparatus and method of the present invention may detect toxins in substances. The toxins may comprise aflatoxins. The aflatoxins may comprise the B1, B2, G1, G2, M1, or M2 variants, or a combination thereof. The substances may originate from bins, aspirator units, conveyor or moving belts, the dynamic headspace above nuts, shells, half-shells, or a combination thereof. The substances may comprise a powder or a powder dissolved in a solvent. The substance may comprise particulate matter or particulate matter dissolved in a solvent. The substance may be dried to form an extract. The drying may occur at room temperature. The substance may be vaporized or made gaseous. The substance may be vaporized or made gaseous by a vacuum, and increased temperature, or a combination thereof. The vaporized or gaseous substance may be contacted with gas ions. The gas ions may comprise, but not be limited to, $^{63}Ni$. The substance may be analyzed for at least about 1 minute, about 1 minute to about 30 minutes, about 5 minutes to about 25 minutes, about 10 minutes to about 20 minutes, or about 30 minutes.

The mass spectral response of aflatoxins may be analyzed with respect to the formation and identity of ions derived from DART ionization. Without being bound by a single theory, an ion at 146 Da may be formed from a constituent of substance (e.g., pistachio) matrices. The 146 Da ion may be attributed to a protonated monomer (i.e., $M^{H+}$, where M is a molecule). The molecule M may have a strong proton affinity which is consistent with a nitrogen-containing substance and the mass may be consistent with a single nitrogen in the substance. The compound may be known from isotropic analysis to contain seven carbon atoms best matching the formula $C_7H_{15}NO_2$ (atomic mass of 145 g/mol). The molecule may be an amino acid or an ion derived from amino acid after heating (at temperatures of at least 300° C.) in the DART ion source. The 146 Da ion may form an adduct with the aflatoxin molecule (e.g., B1, with atomic mass of 314 g/mol) to form an ion at 458 Da. Other aflatoxins with characteristic atomic masses may also form adducts with the 146 Da 1ion. The 458 Da ion may be decomposed using a capillary tube interface before reaching the analyzer of the mass spectrometer.

A 145 Da ion may also be formed from a constituent of substance (e.g., pistachio) matrices. The 145 Da ion and/or 146 Da ion may be an amino acid. The ions may include, but are not limited to, an ion of 2-aminoheptanoic acid, 3-aminohepatanoic acid, 7-aminoheptanoic acid, or a combination thereof.

References to aflatoxins throughout the specification mean aflatoxins in their anionic and/or ionic form and in their natural state and state analyzed through mass spectrometry, HPLC, and/or any other analyzed method.

Multiple substances may be taken sequentially or simultaneously. The apparatus and method may analyze the substances on-site without the need to transport the substances from the agricultural processing site. The substances may be monitored continuously and in real-time. Effective substance monitoring based on dust analysis at the aspirator may prevent high level of toxins from entering an agricultural processing facility. Dust substances be obtained by vacuum trapping or mechanical collection.

The apparatus and method may have a toxin detection limit at about 1.0 ppb. The presence of toxin in substance may be determined in approximately 5 seconds. The substance volume entering the apparatus may be at least about 0.5 µL, about 0.5 µL to about 3 µL, about 1.0 µL to about 2.5 µL, about 1.5 µL to about 2.0 µL, or about 3.

Embodiments of the present invention provide a technology-based solution that overcomes existing problems with the current state of the art in a technical way to satisfy an existing problem for the detection of a substance, e.g., a toxin and/or contaminant, in an agricultural product. Embodiments of the present invention achieve important benefits over the current state of the art, such as increased ease and accuracy in detecting a substance at a production line and/or facility. Some of the unconventional steps of embodiments of the present invention include the combination of DART, a neutral excluder, and a mass spectrometer to detect a substance in solid particulate material.

INDUSTRIAL APPLICABILITY

The invention is further illustrated by the following non-limiting examples.

Example 1

A method for the extraction of nuts and removal of oil was developed. Several methods were evaluated for removing the oils from the dust substances including thin-layer-chromatography (TLC), different extraction methods, and different types of columns. Two types of columns were analyzed. First, immunoaffinity columns specific for aflatoxin were utilized. The columns did work to 'concentrate' aflatoxin. A simple filter column, e.g., alumina, was evaluated and did remove the oils from pistachio dust. Further analysis using pistachio dust spiked with a known amount of standard aflatoxin resulted in less than 10% loss of aflatoxin and removal of the oils.

Calibration curves were completed for several different injection methods for using IMS including electrospray, direct injection using corona discharge, GC-heated port, and paper-spray. The IMS response to aflatoxin shows multiple peaks and/or shifting of peaks depending upon the quantity of aflatoxin. This is typical when using IMS technology. A 'pass-fail' system is useful in accordance with the present invention.

Example 2

An aflatoxin mixture was purchased and analyzed using several different IMS introduction methods. A commercially available product was also used as a control system to validate aflatoxin amounts in substances. The products were aflatoxin test strips which were used to provide test substances to determine if aflatoxin was present at quantities greater than or equal to either 10 ppb or 20 ppb. The difference in the indicated concentration was controlled by the amount of solvent used. The result was not quantitative. For instance, if the substance had 500 ppb aflatoxin, this system told the user that aflatoxin is present at a concentration greater than or equal to the cutoff limit used (10 or 20 ppb). The same result would have been indicated for 21 ppb aflatoxin.

Electrospray IMS (ESI-IMS) was investigated as an introduction method. These results indicated that ESI-IMS is potentially a viable technology for substance introduction. However, ESI-IMS was susceptible to both particulates and oils in the substance matrix and also the need for a longer 'purging' period was found between substances.

The use of a gas chromatograph (GC) heated injection port as the approach to introduce aflatoxin standards to an IMS was investigated. In a GC injection port the solvent and substance were heated to a high temperature with the intent to volatilize the substance and solvent. The volatilized chemicals were then swept into the IMS using a flowing gas stream.

Direct injection with corona discharge was used. This method was shown to detect aflatoxin below the limit of detection needed.

Paper-spray IMS was constructed for introduction of the substance into the IMS. This proved to be a good option if dust is collected on a filter for testing. The inlet system of the present invention eliminated drying of the paper from the heated gas that originated from the IMS. This inlet system has an addition of two exit ports that are connected to a small pump.

Example 3

Standards were prepared to review response over a range of quantities. These standards also served to determine the limit of detection for the instrument.

Based upon the results from instrument procedures, the paper-spray and electrospray substance introduction technologies were transported along with the laboratory bench top IMS. Substances were collected from a pistachio processing facility and then transported back to a portable lab for extraction and analysis. The paper-spray-IMS demonstrated that it was capable of measuring aflatoxin under field conditions. This was correlated with the use of the aflatoxin test strips.

Dust spiked with aflatoxin was placed onto pistachio nuts to look at percentage of aflatoxin recovered for testing. Dust was obtained from beside one of the first conveyor belts early in the processing plant at a farm. The following treatments were then performed for testing the effectiveness of measuring aflatoxin: (1) 200 mg pistachio dust with no added aflatoxin standard; (2) 200 mg pistachio dust with aflatoxin standard added at 40 ppb, added prior to columns; (3) no pistachio dust with aflatoxin standard added at 40 ppb, added prior to columns; (4); 200 mg pistachio dust with 20 ppb aflatoxin standard, added at the end of treatment; and (5) no pistachio dust with 20 ppb aflatoxin standard, added at end of the treatment.

For the test setup, a glass vacuum manifold was assembled and one large UTC enviroclean oil filter column was placed in one of the five inlet ports of the manifold. 1000 μl pipette tips were placed into the top of each filter to act as a holding basin for the liquid to be passed through each filter. Clean 15 ml conical tubes were placed under each port to collect the filtered substances. 200 mg of pistachio dust was weighed out for each of treatments 1,2, and 4. The dust was added to individual 15 ml conical tubes. 4 ml of 70% methanol was added to tubes 1, 2,3, 4, and 5. 4 μl of aflatoxin standard was added to substances 2 and 3. All substances were shaken for one minute. With the vacuum turned on and not exceeding 34 kPa, 2 ml of each substance were passed through each corresponding filter and collected in the conical tubes below. 2 μl of aflatoxin standard was added to substances 4 and 5. All substances were mixed gently. 250 μl of each substance was transferred into an individual epi tube. 250 μl of deionized water was also added to each epi tube and mixed gently using the pipette. A test strip was added to each epi tube and allowed to develop for fifteen minutes.

The pistachio dust alone did not have aflatoxin levels at or higher than 20 ppb. The spiked substances all tested positive and it was inferred from these results that there was minimal loss of aflatoxin during the process. Overall, this test concluded that the extraction process designed to remove aflatoxin from pistachio dust was effective and did appear to give an accurate quantification of the amount of aflatoxin present in the original substance.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited.

Although the invention has been described in detail with particular reference to these embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for detecting a substance, said apparatus comprising:

a direct analysis in real time apparatus;

a neutral excluder in communication with said direct analysis in real time apparatus; and said neutral excluder charged by an electrode.

2. The apparatus of claim 1 further comprising a separator in communication with said neutral excluder.

3. The apparatus of claim 1 further comprising a mass spectrometer in communication with said neutral excluder.

4. The apparatus of claim 1 further comprising a vessel in communication with said neutral excluder.

5. The apparatus of claim 1 further comprising a gas.

6. The apparatus of claim 5 wherein said gas comprises air.

7. The apparatus of claim 1 further comprising an alcohol.

8. The apparatus of claim 1 further comprising a filter in communication with said neutral excluder.

9. The apparatus of claim 1 further comprising a pump in communication with said neutral excluder.

10. The apparatus of claim 1 further comprising an electrode in communication with said direct analysis in real time apparatus.

11. The apparatus of claim 1 further comprising an electrode in communication with said neutral excluder.

12. The apparatus of claim 1 wherein said neutral excluder further comprises an insulator.

13. The apparatus of claim 1 wherein said substance comprises a dust.

14. A method for detecting a substance, the method comprising:

contacting the substance with a direct analysis in real time apparatus ion stream;

ionizing the substance to form an ion and a neutral particle;

flowing the ion and the neutral particle into a neutral excluder, wherein said neutral excluder is charged by an electrode; and separating an ion from the neutral particle.

15. The method of claim 14 further comprising contacting the ion and the neutral particle with a gas.

16. The method of claim 15 wherein the gas comprises air.

17. The method of claim 14 further comprising flowing the ion into a mass spectrometer.

18. The method of claim 14 further comprising flowing the substance into a separator.

19. The method of claim 14 further comprising applying a current to the neutral excluder.

\* \* \* \* \*